United States Patent
Lee et al.

(10) Patent No.: US 10,270,114 B2
(45) Date of Patent: Apr. 23, 2019

(54) ELECTROLYTE FOR LITHIUM AIR BATTERY AND LITHIUM AIR BATTERY INCLUDING THE SAME

(71) Applicant: Samsung Electronics Co., Ltd., Suwon-si, Gyeonggi-do (KR)

(72) Inventors: Dongjoon Lee, Suwon-si (KR); Eunha Park, Seoul (KR); Kihyun Kim, Seoul (KR); Taeyoung Kim, Seoul (KR); Victor Roev, Suwon-si (KR); Hyunpyo Lee, Seoul (KR); Heungchan Lee, Seongnam-si (KR); Dongmin Im, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 402 days.

(21) Appl. No.: 15/161,682

(22) Filed: May 23, 2016

(65) Prior Publication Data
US 2017/0092973 A1 Mar. 30, 2017

(30) Foreign Application Priority Data
Sep. 25, 2015 (KR) .................. 10-2015-0137094

(51) Int. Cl.
*H01M 8/1016* (2016.01)
*C07C 211/63* (2006.01)
(Continued)

(52) U.S. Cl.
CPC ......... *H01M 8/1016* (2013.01); *C07C 211/63* (2013.01); *C07C 311/48* (2013.01);
(Continued)

(58) Field of Classification Search
None
See application file for complete search history.

(56) References Cited

U.S. PATENT DOCUMENTS 6,743,947 B1 6/2004 Xu et al.
2004/0222401 A1* 11/2004 Xu .................. C07D 213/20
252/62.2
(Continued)

FOREIGN PATENT DOCUMENTS

CN 104496928 A 4/2015
JP 2005026023 A 6/2003
(Continued)

OTHER PUBLICATIONS

European Search Report for European Patent Application No. 16184272.9 dated Jan. 4, 2017.
(Continued)

*Primary Examiner* — Wyatt P McConnell
(74) *Attorney, Agent, or Firm* — Cantor Colburn LLP

(57) ABSTRACT

An electrolyte for a lithium air battery includes a compound represented by Formula 1

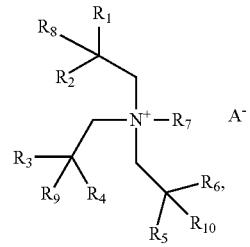

Formula 1 wherein the definitions of A and $R_1$-$R_{10}$ are disclosed herein. Also a lithium air battery including an anode, a cathode, and
(Continued)

at least one selected from the herein-described electrolyte and a reaction product thereof.

19 Claims, 8 Drawing Sheets

(51) Int. Cl.
    *C07C 311/48*     (2006.01)
    *H01M 12/08*     (2006.01)
    *H01M 10/0569*     (2010.01)
    *H01M 8/1018*     (2016.01)

(52) U.S. Cl.
    CPC ....... *H01M 10/0569* (2013.01); *H01M 12/08* (2013.01); *H01M 2008/1095* (2013.01); *H01M 2300/0025* (2013.01); *Y02E 60/128* (2013.01)

(56) References Cited

U.S. PATENT DOCUMENTS

2011/0294021 A1* 12/2011 Suto ............... H01M 12/02
                                                         429/403

2013/0323571 A1   12/2013  Dai et al.
2014/0004428 A1    1/2014  Nakamoto
2014/0295292 A1   10/2014  Nakamoto

FOREIGN PATENT DOCUMENTS

| | | |
|---|---|---|
| JP | 2009105028 A | 5/2009 |
| JP | 2011-014478 A | 1/2011 |
| JP | 2013-084430 A | 5/2013 |
| JP | 2013084432 A | 5/2013 |
| JP | 5598503 B2 | 8/2014 |
| KR | 1020110025661 A | 3/2011 |
| KR | 1020110026661 A | 3/2011 |
| WO | 2010095082 A1 | 8/2010 |

OTHER PUBLICATIONS

Lang et al., "Development of Quaternary Ammonium Based Electrolytes for Rechargeable Batteries and Fuel Cells", Georgia Inst of Technology, Dec. 2006.

Zhang et al., "The effect of quaternary ammonium on discharge characteristic of a non-aqueous electrolyte Li/O2 battery", Electrochimica Acta, 56, 2011, pp. 1283-1287.

* cited by examiner

ELECTROLYTE FOR LITHIUM AIR BATTERY AND LITHIUM AIR BATTERY INCLUDING THE SAME

CROSS-REFERENCE TO RELATED APPLICATION

This application claims the benefit of and priority to Korean Patent Application No. 10-2015-0137094, filed on Sep. 25, 2015, in the Korean Intellectual Property Office, and all the benefits accruing therefrom under 35 U.S.C. § 119, the content of which is incorporated herein in its entirety by reference.

BACKGROUND

1. Field

The present disclosure relates to an electrolyte for a lithium air battery, and a lithium air battery including the same.

2. Description of the Related Art

A lithium air battery includes an anode, a cathode that uses oxygen in the air as a cathode active material and includes a catalyst for oxidizing and reducing oxygen, and a lithium ion-conductive electrolyte disposed between the cathode and the anode.

Lithium air batteries have a theoretical energy density about ten times greater than that of lithium ion batteries. Furthermore, because lithium air batteries are more environmentally friendly and safer in use than lithium ion batteries, lithium air batteries are increasingly being developed. Such lithium air batteries may use a non-aqueous electrolyte or an aqueous electrolyte as a lithium ion-conductive medium.

Lithium ions generated in an anode during discharging may form a lithium oxide ($Li_2O_2$) by reaction with oxygen migrating from a cathode. This lithium oxide is non-conductive and unstable and may react with the electrolyte. The electrolyte may become severely decomposed during discharging under an oxygen atmosphere and high-voltage conditions, consequentially deteriorating performance of the lithium air battery. Therefore, there is a need for an improved lithium air battery.

SUMMARY

Provided is an electrolyte with improved stability for a lithium air battery.

Provided is a lithium air battery with improved stability including the electrolyte.

Additional aspects will be set forth in part in the description which follows and, in part, will be apparent from the description, or may be learned by practice of the presented exemplary embodiments.

According to an aspect of an exemplary embodiment, an electrolyte for a lithium air battery includes a compound represented by Formula 1:

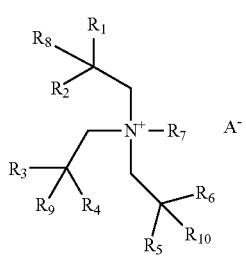

Formula 1 wherein, in Formula 1, $R_1$ to $R_6$ are each independently a substituted or unsubstituted C1-C10 alkyl group, $R_7$ is a substituted or unsubstituted C1-C10 alkyl group, $R_8$, $R_9$, and $R_{10}$ are each independently a hydrogen or substituted or unsubstituted C1-C10 alkyl group, a total number of carbons of $R_1$, $R_2$, and $R_8$ is 6 to 30, a total number of carbons of $R_3$, $R_4$, and $R_9$ is 6 to 30, a total number of carbons of $R_5$, $R_6$, and $R_{10}$ is 3 to 20, and $A^-$ is a monovalent anion.

According to an aspect of another exemplary embodiment, a lithium air battery includes: an anode; a cathode; and at least one selected from the electrolyte and a reaction product thereof.

BRIEF DESCRIPTION OF THE DRAWING

These and/or other aspects will become apparent and more readily appreciated from the following description of the exemplary embodiments, taken in conjunction with the accompanying drawings in which.

DETAILED DESCRIPTION

Figure 1:
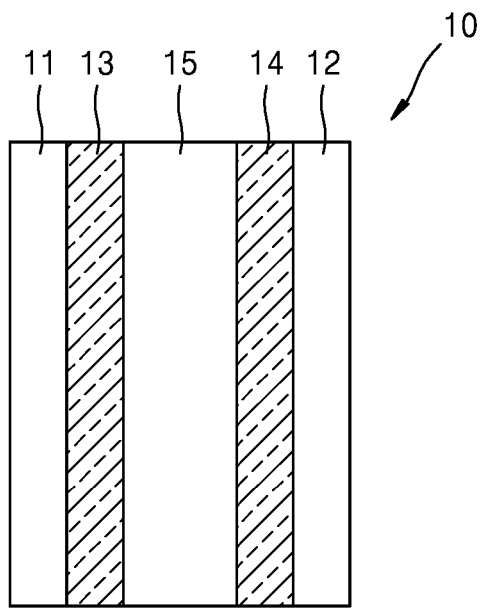
FIG. 1 is a schematic view of a lithium air battery according to an embodiment.

Reference will now be made in detail to exemplary embodiments of an electrolyte for a lithium air battery, and a lithium air battery including the same, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. "Or" means "and/or." As used herein, the term "and/or" includes any and all combinations of one or more of the associated listed. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third," etc. may be used herein to describe various elements, components, regions, layers, and/or sections, these elements, components, regions, layers, and/or sections should not be limited by these terms. These terms are only used to distinguish one element, component, region, layer or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an". It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect of the present disclosure, an electrolyte for a lithium air battery includes a compound represented by Formula 1, Formula 1

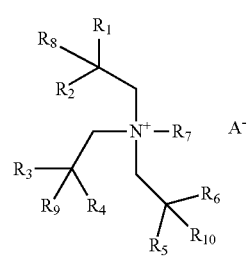

wherein, in Formula 1, $R_1$ to $R_6$ are each independently a substituted or unsubstituted C1-C10 alkyl group. In an embodiment, $R_1$ to $R_6$ may each independently be a C1-C10 alkyl group. In Formula 1, $R_1$ to $R_6$ may each independently be a methyl group, an ethyl group, a propyl group, an isopropyl group, an n-butyl group, a tert-butyl group, a sec-butyl group, an isobutyl group, an n-pentyl group, or an isopentyl group. Specifically mentioned is an embodiment wherein $R_1$, $R_3$, and $R_5$ are each independently methyl or ethyl, and $R_2$, $R_4$, and $R_6$ are each independently methyl, isopropyl, or n-butyl.

$R_7$ is a substituted or unsubstituted C1-C10 alkyl group. In an embodiment, $R_7$ is a C1-C10 alkyl group. For example, $R_7$ may be a methyl group, an ethyl group, a propyl group, an n-butyl group, an n-pentyl group, an n-hexyl group, or an n-octyl group. Mentioned is an embodiment in which $R_7$ is methyl, ethyl, n-propyl, or n-octyl.

$R_8$, $R_9$, and $R_{10}$ are each independently a hydrogen or a substituted or unsubstituted C1-C10 alkyl group. In an embodiment, $R_8$, $R_9$, and $R_{10}$ are each independently a hydrogen or a C1-C6 alkyl group. In an embodiment, $R_8$, $R_9$, and $R_{10}$ are each independently a hydrogen or a C1-C10 alkyl group. Mentioned is an embodiment in which $R_8$, $R_9$, and $R_{10}$ are each independently hydrogen or methyl.

A total number of carbons of $R_1$, $R_2$, and $R_8$ may be 6 to 30, and a total number of carbons of $R_3$, $R_4$, and $R_9$ may be 6 to 30, and a total number of carbons of $R_5$, $R_6$, and $R_{10}$ may be 3 to 20.

$A^-$ may be a monovalent anion. In Formula 1, $A^-$ may be at least one selected from $BF_4^-$, $PF_6^-$, $ASF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$ $(CF_3)_4PF_2^-$ $(CF_3)_5PF^-$ $(CF_3)_6P^-$ $SF_5CF_2SO_3^-$, $SF_5CHFCF_2SO_3^-$, $CF_3CF_2(CF_3)_2CO^-$ $(CF_3SO_2)_2CH^-$, $(SF_5)_3C^-$, and $(O(CF_3)_2C_2(CF_3)_2O)_2PO^-$.

The electrolyte may have improved stability with improved oxidation resistance and oxygen affinity, due to the compound represented by Formula 1 in which at least two, for example, or all the three of the substituents bound to nitrogen of the ammonium ions may be a C6-C40 branched alkyl group, for example a C8-C30 branched alkyl group, or a C8-C20 branched alkyl group. As used herein, the term "oxidation resistance" refers to resistance against oxidation of the electrolyte caused by a potential difference between the electrodes or by reaction with a material resulting in oxidation of lithium ions.

For example, the compound represented by Formula 1 may be a compound represented by Formula 2.

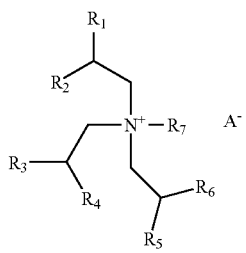

Formula 2 wherein, in Formula 2, $R_1$ to $R_6$ may each independently be a C2-C10 alkyl group;

$R_7$ may be a C1-C10 alkyl group;

a total number of carbons of $R_1$ and $R_2$ is 6 to 20 and a total number of carbons of $R_3$ and $R_4$ is 6 to 20;

a total number of carbons of $R_5$ and $R_6$ may be 3 to 20; and $A^-$ may be at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

In Formula 2, a total number of carbons of $R_5$ and $R_6$ in Formula 2 may be 6 to 20.

For example, the compound represented by Formula 1 may be at least one selected from compounds represented by Formulas 3 to 6:

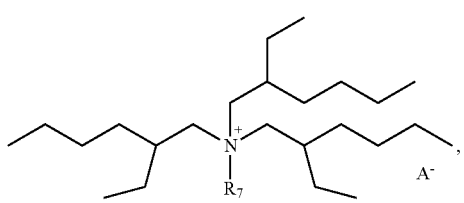

Formula 3

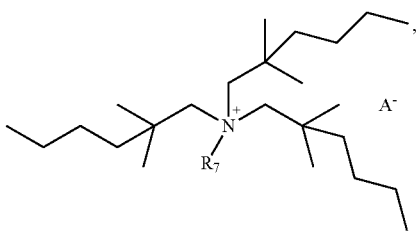

Formula 4

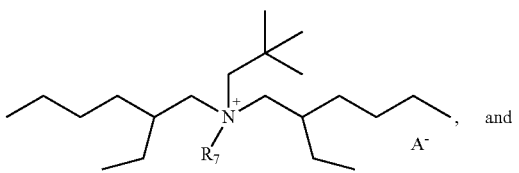

Formula 5

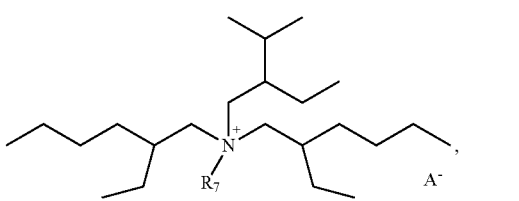

Formula 6 wherein, in Formulas 3 to 6, $R_7$ may be a C1-C10 alkyl group, and $A^-$ may be a monovalent anion, for example, at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$(hereinafter, also referred to as "TFSI$^-$"), $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^{31}$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

In some embodiments, the compound represented by Formula 1 may be at least one selected from compounds represented by Formulas 7 to 13:

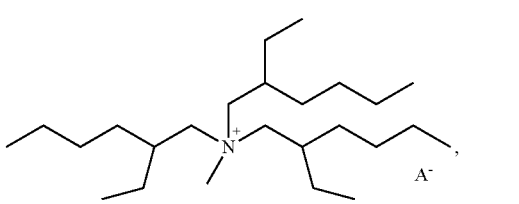

Formula 7

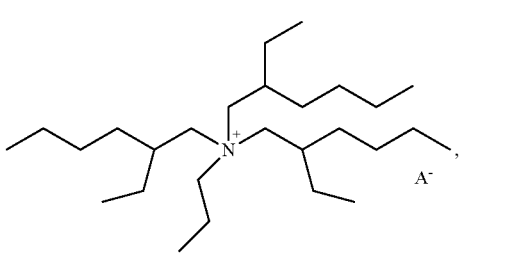

Formula 8

Formula 9

Formula 10

Formula 11

Formula 12

Formula 13 wherein, in Formulas 7 to 13, $A^-$ may be at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, and $(SF_5)_3C^-$, $(O(CF_3)_2C_2(CF_3)_2O)_2PO^-$.

For example, in Formulas 7, to 13, $A^-$ may be a sulfonyl imide anion such as $(CF_3SO_2)_2N^-$, $(FSO_2)_2N^-$, $(C_2F_5SO_2)_2N^-$, or $(C_2F_5SO_2)(CF_3SO_2)N^-$.

In some embodiments, the compound represented by Formula 1 may be at least one selected from compounds represented by Formulas 7a to 13a:

Formula 7a

Formula 8a

Formula 9a

Formula 10a

Formula 11a

-continued

Formula 12a

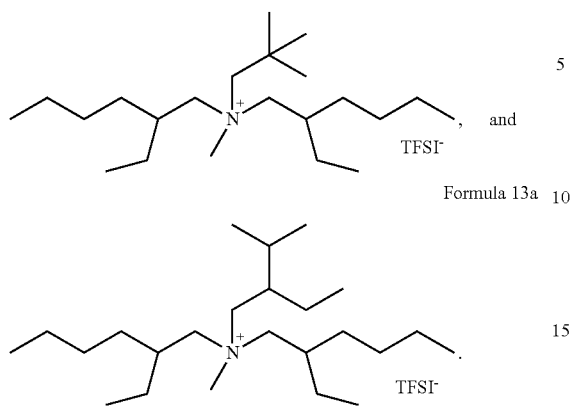

Formula 13a

In Formulas 7a to 13a, TFSI⁻, represents a trifluoromethyl-sulfonylimide ion.

Hereinafter, a mechanism of ionic liquid deterioration and the mechanism of stability improvement by suppressed deterioration and decomposition of the compound represented by Formula 1 will be further described, which is only for illustrative purposes and is not intended to limit the scope of the present disclosure. The compound represented by Formula 1 is used as an ionic liquid.

For example, and while not wanting to be bound by theory, decomposition of a cation of an ionic liquid under alkaline conditions may be explained with alpha position attack at alpha carbon of nitrogen, as illustrated in Reaction Scheme 1.

Reaction Scheme 1

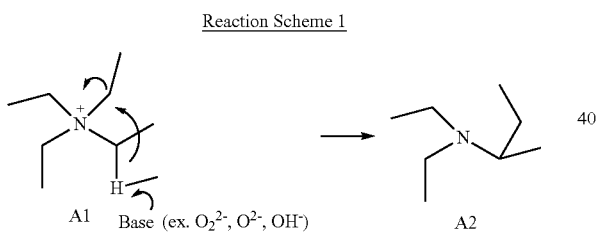

As illustrated in Reaction Scheme 1, a Stevens rearrangement may occur as a hydrogen (H) at an alpha carbon position of an ammonium ion (A1) is attacked by an external base to form an amine (A2).

As another example, decomposition of a cation of an ionic liquid under alkaline conditions may be explained with alpha position attack at alpha carbon of nitrogen, as illustrated in Reaction Scheme 2. As illustrated in Reaction Scheme 2, an ammonium ion (A3) may undergo a substitution reaction with an external base to form an amine (A4).

Reaction Scheme 2

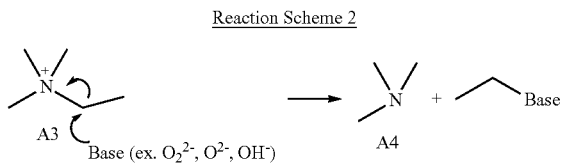

As still another example, decomposition of a cation of an ionic liquid under alkaline conditions may occur via abstraction of a hydrogen at a beta carbon relative to nitrogen, to form an amine. For example, as illustrated in Reaction Scheme 3 below, Reaction Scheme 3

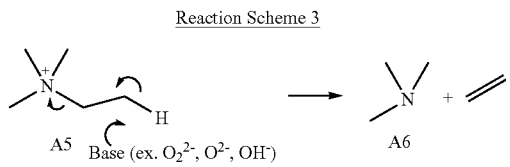

an elimination reaction of an ammonium ion (A5) may occur as a hydrogen (H) at beta carbon position of the ammonium ion (A5) is attacked by an external base, which consequentially leads to decomposition of the ionic liquid and formation of an amine (A6).

However, in the electrolyte according to an embodiment, the compound represented by Formula 2 may have an alkyl group of C8 or greater, for example, a C8 or greater branched bulky alkyl group bound to an ammonium ion, and the steric hindrance of this bulky alkyl group may block an attack of an external base, as illustrated in Reaction Scheme 4. In other words, the alpha position attack of Reaction Schemes 1 and 2 and the beta position attack of Reaction Scheme 3 may be effectively suppressed, so that the compound represented by Formula 1 may have improved stability.

Reaction Scheme 4

Formula 2

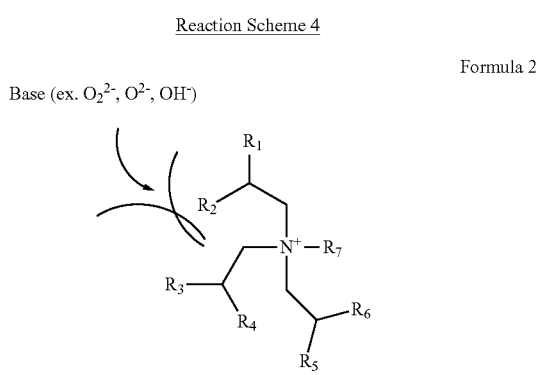

In Formula 2 of Reaction Scheme 4, $R_1$ to $R_7$ may be defined the same as described above.

In Formula 2 of Reaction Scheme 4, $R_7$ may be, for example, a methyl group, an ethyl group, an n-propyl group, an n-butyl group, an n-pentyl group, an n-hexyl group, or an n-octyl group. In other words, $R_7$ may be an alkyl group with relatively small steric hindrance compared to $R_1$, $R_2$, $R_3$, $R_4$, $R_5$, and $R_6$ bound to nitrogen of the ammonium ion, in order to facilitate synthesis of the compound of Formula 1.

In some embodiments, the amount of the compound represented by Formula 1 in the electrolyte may be in a range of about 15 parts to 97 parts by weight, for example, about 30 parts to about 90 parts by weight, or about 40 parts to about 80 parts by weight, based on 100 parts by weight of a total weight of the electrolyte. When the amount of the compound represented by Formula 1 is within any of these ranges, the electrolyte may have improved oxidation resistance.

In some embodiments, the electrolyte may further include a lithium salt. The lithium salt may serve as a source of lithium ions by being dissolved in an organic solvent. For example, the lithium salt may be at least one selected from LiPF$_6$, LiBF$_4$, LiSbF$_6$, LiAsF$_6$, LiN(SO$_2$C$_2$F$_5$)$_2$, Li(CF$_3$SO$_2$)$_2$N, LiC$_4$F$_9$SO$_3$, LiClO$_4$, LiAlO$_2$, LiAlCl$_4$, LiN(C$_x$F$_{2x+1}$SO$_2$)(C$_y$F$_{2y+1}$SO$_2$) wherein x and y are natural numbers, LiF, LiBr, LiCl, LiOH, LiI, LiB(C$_2$O$_4$)$_2$, lithium bis(oxalato) borate, Li(FSO$_2$)$_2$N, Li(CF$_3$SO$_2$)$_2$N, Li(C$_2$F$_5$SO$_2$)$_2$N, LiN(C$_p$F$_{2p+1}$SO$_2$)(C$_q$F$_{2q+1}$SO$_2$) wherein p and q differ from each other and are each independently an integer of 1 to 20, LiN((SO$_2$)$_2$C$_p$F$_{2p}$) wherein p is an integer selected from 1 to 10, Li(C$_6$F$_5$SO$_2$)$_2$N, Li(C$_{10}$F$_7$SO$_2$)$_2$N, Li(C$_6$F$_5$SO$_2$)(C$_{10}$F$_7$SO$_2$)N, LiN(C$_6$F$_5$SO$_2$)(C$_p$F$_{2p+1}$SO$_2$) wherein p is an integer of 1 to 10, and LiN(C$_{10}$F$_7$SO$_2$)(C$_p$F$_{2p+1}$SO$_2$) wherein p is an integer of 1 to 10.

In some embodiments, the amount of the lithium salt may be in a range of about 0.01M to about 10M, for example, about 0.1M to about 5M, or about 0.1M to about 2.0M. When the amount of the lithium salt is within any of these ranges, the electrolyte may have improved performance with appropriate conductivity and viscosity, and may lead to effective migration of lithium ions.

In some embodiments, the electrolyte may further include a metal salt, in addition to a lithium salt, for example, AlCl$_3$, MgCl$_2$, NaCl, KCl, NaBr, KBr, CaCl$_2$, or the like.

In some embodiments, the electrolyte may further include a nonaqueous organic solvent. The nonaqueous organic solvent may be a carbonate solvent, an ester solvent, an ether solvent, a ketone solvent, an amine solvent, or a phosphine solvent.

Non-limiting examples of the carbonate solvent include dimethyl carbonate (DMC), diethyl carbonate (DEC), ethyl methyl carbonate (EMC), dipropyl carbonate (DPC), methylpropyl carbonate (MPC), ethyl propyl carbonate (EPC), methyl ethyl carbonate (MEC), ethylene carbonate (EC), propylene carbonate (PC), and butylene carbonate (BC).

Non-limiting examples of the ester solvent include methyl acetate, ethyl acetate, n-propyl acetate, dimethyl acetate, methyl propionate, ethyl propionate, γ-butyrolactone, decanolide, valerolactone, mevalonolactone, and caprolactone.

Non-limiting examples of the ether solvent include dibutyl ether, tetraglyme, diglyme, dimethoxyethane, 2-methyltetrahydrofuran, and tetrahydrofuran. An example of the ketone solvent is cyclohexanone.

Non-limiting examples of the amine solvent include triethylamine and triphenylamine. An example of the phosphine solvent is triethylphosphine. However, embodiments are not limited thereto, and any aprotic solvents available in the art may be used.

Non-limiting examples of the aprotic solvent include nitriles, such as R—CN (wherein R is a straight, branched or cyclic C2-C30 hydrocarbon group, which may have a double bond, an aromatic ring, or an ether bond); amides, such as dimethylformamide; dioxolanes, such as 1,3-dioxolane; and sulfolanes.

These aprotic solvents may be used alone or in combination of at least two thereof. A mixing ratio of at least two of the aprotic solvents may be appropriately varied depending on the desired performance of a battery, the details of which can be determined by one of skill in the art without undue experimentation.

Non-limiting examples of the nonaqueous organic solvent include methylbutyl ether, diethyl ether, ethyl butyl ether, dibutyl ether, polyethylene glycol dimethyl ether, tetraethylene glycol dimethyl ether; cyclohexanone, dioxane; dimethoxyethane, 2-methyltetrahydrofuran, 2,2-dimethyltetrahydrofuran, 2,5-dimethyltetrahydrofuran, tetrahydrofuran; dimethyl acetate, ethyl acetate, n-propyl acetate, dimethyl acetate, methyl propionate, ethyl propionate; methyl formate, or ethyl formate; dimethyl carbonate, diethyl carbonate, ethyl methyl carbonate, dipropyl carbonate, methyl propyl carbonate, ethyl propyl carbonate, ethylene carbonate, propylene carbonate, butylene carbonate, polyethylene carbonate; γ-butyrolactone, decanolide, valerolactone, mevalonolactone, caprolactone; diglyme, triglyme, tetraglyme; acetonitrile, benzonitrile, nitromethane, nitrobenzene, triethylamine, triphenylamine, tetraethylene glycol diamine; dimethylformamide, diethylformamide, N-methylpyrrolidone; dimethyl sulfone, tetramethylene sulfone, triethylphosphine oxide, 1,3-dioxolane, and sulfolane.

In some embodiments, when analyzed by liquid chromatography-mass spectrometry in a positive ion mode, the electrolyte may exhibit a molecular ion peak from mass/atomic number (m/z) 320 to m/z 1090. The LC-MS is measured using an Orbitrap Velos Pro Orbitrap Elite.

In some embodiments, the electrolyte may further include a lithium ion-conductive polymer, in addition to the compound represented by Formula 1. The lithium ion-conductive polymer may include a hydrophilic matrix polymer having lithium ion conductivity.

For example, the hydrophilic matrix polymer may be at least one selected from an alkylene oxide polymer, a hydrophilic acrylic polymer, and a hydrophilic methacrylic polymer.

The alkylene oxide polymer refers to a polymer having an alkylene oxide molecular chain with alternately arranged alkyl group and ether oxygen. For example, the alkylene oxide polymer may be at least one selected from a polypropylene oxide, a polyethylene oxide, and a polyethylene oxide/polypropylene oxide copolymer.

In some embodiments, the lithium ion-conductive polymer may have a weight average molecular weight of about 2,000 or greater, and in some other embodiments, about 2,000 Daltons to about 1,000,000 Daltons, about 3000 Daltons to about 500,000 Daltons, or about 4000 Daltons to about 100,000 Daltons. However, embodiments are not limited thereto. The lithium ion-conductive polymer may have a weight average molecular weight within any range to suppress growth of lithium dendrite in a battery.

The hydrophilic acrylic polymer and the hydrophilic methacrylic polymer refer to an acrylic polymer and a methacrylic polymer, respectively, each having a hydrophilic group. The hydrophilic group may be any functional group that may offer hydrophilicity, for example, a phosphoric acid group or a sulfonic acid group.

For example, the lithium ion-conductive polymer may include polyethylene oxide, polyacrylonitrile, or polyester.

In some embodiments, the electrolyte may be used in, for example, a lithium secondary battery or a lithium air battery.

According to another aspect, a lithium air battery includes: an anode; a cathode; and at least one selected from an electrolyte according to any of the above-described embodiments and a reaction product thereof.

In the cathode, oxygen is used as a cathode active material

In some embodiments, the electrolyte of the lithium air battery may further include a lithium salt.

In some embodiments, the lithium air battery may further include a lithium ion-conductive layer between the anode and the electrolyte, wherein the lithium ion-conductive layer includes an ion-conductive inorganic particle. The ion-conductive inorganic particle may include at least one selected from a glassy active metal ion conductor, an amorphous active metal ion conductor, a ceramic active metal ion conductor, and a glass-ceramic active metal ion conductor. For example, the ion-conductive inorganic particle may be at least one selected from $Li_{1+x+y}Al_xTi_{2-x}Si_yP_{3-y}O_{12}$ wherein $0<x<2$ and $0\leq y<3$, $BaTiO_3$, $Pb(Zr_aTi_{1-a})O_3$ (PZT) wherein $0\leq a\leq 1$, $Pb_{1-x}La_xZr_{1-y}Ti_yO_3$ (PLZT) wherein $0\leq x<1$ and $0\leq y<1$, $Pb(Mg_{3}Nb_{2/3})O_3$—$PbTiO_3$ (PMN-PT), $HfO_2$, $SrTiO_3$, $SnO_2$, $CeO_2$, $Na_2O$, $MgO$, $NiO$, $CaO$, $BaO$, $ZnO$, $ZrO_2$, $Y_2O_3$, $Al_2O_3$, $TiO_2$, $SiO_2$, SiC, lithium phosphate ($Li_3PO_4$), lithium titanium phosphate, $Li_xTi_y(PO_4)_3$ wherein $0<x<2$ and $0<y<3$, lithium aluminum titanium phosphate, $Li_xAl_yTi_z(PO_4)_3$ wherein $0<x<2$, $0<y<1$, and $0<z<3$, $Li_{1+x+y}(Al_bGa_{1-b})_x(Ti_cGe_{1-c})_{2-x}Si_yP_{3-y}O_{12}$ (Oy, Ge) wherein $0<y<1$, lithium lanthanum titanate, $Li_xLa_yTiO_3$, wherein $0<x<2$, $0<y<3$, $0\leq b\leq 1$ and $0\leq c\leq 1$, lithium germanium thiophosphate, $Li_xGe_yP_zS_w$, wherein $0<x<4$, $0<y<1$, $0<z<1$, and $0<w<5$, lithium nitride, $Li_xN_y$, wherein $0<x<4$ and $0<y<2$, $SiS_2$ glass ($Li_xSi_yS_z$) wherein $0<x<3$, $0<y<2$, and $0<z<4$, $P_2S_5$ glass ($Li_xP_yS_z$) wherein $0<x<3$, $0<y<3$, and $0<z<7$, $Li_2O$, LiF, LiOH, $Li_2CO_3$, $LiAlO_2$, $Li_2O$—$Al_2O_3$—$SiO_2$—$P_2O_5$—$TiO_2$—$GeO_2$ ceramics, and Garnet ceramics ($Li_{3+x}La_3M_2O_{12}$) wherein $0\leq x\leq 5$ and M is Te, Nb, or Zr.

In some embodiments, the lithium air battery may further include a second electrolyte disposed between the anode and the lithium ion-conductive layer. For example, the second electrolyte may be a solid polymer electrolyte or an inorganic solid electrolyte.

In some embodiments, the solid polymer electrolyte may be, for example, a polyethyleneoxide membrane, a polyacrylonitrile membrane, or a polyester membrane. For example, the solid polymer electrolyte may be prepared by mixing a lithium ion-conductive polymer and a lithium salt. For example, the lithium salt may be at least one selected from $LiPF_6$, $LiBF_4$, $LiSbF_6$, $LiAsF_6$, $LiN(SO_2C_2F_5)_2$, $Li(CF_3SO_2)_2N$, $LiC_4F_9SO_3$, $LiClO_4$, $LiAlO_2$, $LiAlCl_4$, $LiN(C_xF_{2x+1}SO_2)(C_yF_{2y+1}SO_2)$ wherein x and y are natural numbers, LiF, LiBr, LiCl, LiI, and $LiB(C_2O_4)_2$, lithium bis(oxalato) borate, LiBOB. In some embodiments, the inorganic solid electrolyte may be, for example, $Cu_3N$, $Li_3N$, or LiPON.

FIG. 1 is a schematic view of a lithium air battery 10 according to an embodiment. Referring to FIG. 1, the lithium air battery 10 includes a first current collector 11, a second current collector 12, a cathode 13, an anode 14, and an electrolyte including a compound of Formula 1 as described above (hereinafter, referred to as "first electrolyte 15") disposed between the cathode 13 and the anode 14. The cathode 13 may be on the first current collector 11. In the cathode 13, oxidation and reduction of oxygen used as an active material take place. The anode 14 may be on the second current collector 12. In the anode 14, oxidation and reduction of lithium metal take place. The first electrolyte 15 may enable conduction of lithium ions between the cathode 13 and the anode 14.

A porous structure in a net shape or mesh shape may be used as the first and second current collectors 11 and 12 to facilitate diffusion of oxygen. For example, a porous metal plate made of, for example, stainless steel, nickel, or aluminum may be used as the first and second current collectors 11 and 12. Materials for the first and second current collectors 11 and 12 are not particularly limited, and any suitable materials for current collectors available in the art may be used. The first and second current collectors 11 and 12 may be coated with an anti-oxidation metal or an alloy thereof to prevent oxidation.

The cathode 13 using oxygen as a cathode active material may include a porous conductive material. Any porous and conductive material, for example, a porous carbonaceous material, may be used without limitations as the cathode 13. Suitable porous carbonaceous materials may be carbon black, graphite, graphene, activated carbon, carbon nanotubes, and carbon fibers. A metallic conductive material, for example, metal fiber, metal mesh, or the like, may be used as the cathode 13. For example, metal powder of copper, silver, nickel, aluminum, or the like may be used as the cathode 13. Organic conductive materials such as polyphenylene derivatives may also be used as the cathode 13. The above-listed conductive materials may be used alone or in combination.

The cathode 13 may further include a catalyst for facilitating oxidation or reduction of oxygen. Non-limiting examples of the catalyst include precious metal-based catalysts, such as platinum (Pt), gold (Au), silver (Ag), palladium (Pd), ruthenium (Ru), rhodium (Rh), and osmium (Os); oxide-based catalysts, such as manganese oxide, iron oxide, cobalt oxide, and nickel oxide; and organic metal-based catalysts, such as cobalt phthalocyanine. Any appropriate catalysts for oxidation and reduction of oxygen available in the art may be used.

The catalyst may be supported on a support. Non-limiting examples of the support include oxide, zeolite, clay mineral, and carbon. The oxide may include at least one oxide of alumina, silica, zirconium oxide, and titanium dioxide. The oxide may be an oxide that includes at least one metal selected from cerium (Ce), praseodymium (Pr), samarium (Sm), europium (Eu), terbium (Tb), thulium (Tm), ytterbium (Yb), antimony (Sb), bismuth (Bi), vanadium (V), chromium (Cr), manganese (Mn), iron (Fe), cobalt (Co), nickel (Ni), copper (Cu), niobium (Nb), molybdenum (Mo), and tungsten (W). Non-limiting examples of the carbon include carbon black, such as Ketjen black, acetylene black, channel black, and lamp black; graphite, such as natural graphite, artificial graphite, and expanded graphite; activated carbon; and carbon fibers. Any appropriate materials available as supports in the art may be used.

The cathode 13 may further include a binder. The binder may include a thermoplastic polymer or a thermocurable resin. Non-limiting examples of the binder include polyethylene, polypropylene, polytetrafluoroethylene (PTFE), polyvinylidene fluoride (PVDF), styrene-butadiene rubber, a tetrafluoroethylene-perfluoroalkyl vinyl ether copolymer, a vinylidene fluoride-hexafluoropropylene copolymer, a vinylidene fluoride-chlorotrifluoroethylene copolymer, an ethylene-tetrafluoroethylene copolymer, polychlorotrifluoroethylene, a fluorovinylidene-pentafluoropropylene copolymer, a propylene-tetrafluoroethylene copolymer, an ethylene-chlorotrifluoroethylene copolymer, a vinylidene fluoride-hexafluoropropylene-tetrafluoroethylene copolymer, a vinylidene fluoride-perfluoromethylvinylether-tetrafluoro ethylene copolymer, and an ethylene-acrylic acid copolymer, which may be used alone or in combination. Any appropriate binders available in the art may be used.

The cathode 13 may be manufactured as follows. For example, a catalyst for oxidation/reduction of oxygen, a conductive material, and a binder may be mixed together, and then an appropriate solvent may be added thereto to prepare a cathode slurry. The cathode slurry may be coated and dried on a surface of the first current collector 11, optionally followed by press-molding to improve the density of the cathode 13, thereby manufacturing the cathode 13. Optionally, the cathode 13 may include a lithium oxide. Optionally, the cathode 13 may not include the catalyst for oxidation/reduction of oxygen.

The anode 14 may be any suitable anode material available in the art including, but not limited to, lithium metal, a lithium metal-based alloy, or a material that allows intercalation and deintercalation of lithium ions. The anode 14 may determine the capacity of the lithium air battery 10.

For example, the anode 14 may be, for example, a lithium metal thin film. The lithium metal-based alloy may be, for example, an alloy of lithium with aluminum (Al), tin (Sn), magnesium (Mg), indium (In), calcium (Ca), titanium (Ti), or vanadium (V).

The porous cathode 13 may be fully or partially impregnated with the first electrolyte 15.

Although not illustrated in FIG. 1, a separator may be disposed between the cathode 13 and the anode 14. The separator is not specifically limited, as long as it has a composition durable under the operating conditions of the lithium air battery. For example, the separator may be a polymer non-woven fabric, such as a polypropylene non-woven fabric or a polyphenylene sulfide non-woven fabric, or a porous film of an olefin polymer, such as polypropylene or polyethylene, which may be used in a combination of at least two thereof.

Figure 2:
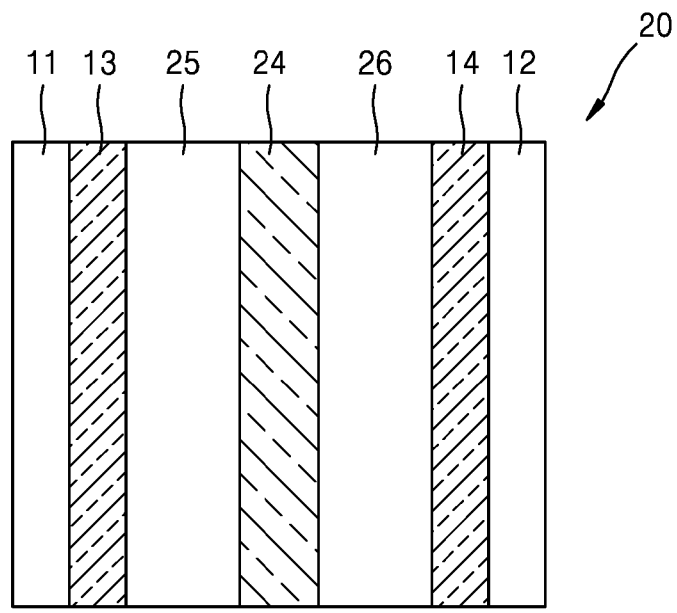
FIG. 2 is a schematic view illustrating a structure of a lithium air battery 20 according to another embodiment.

FIG. 2 is a schematic view illustrating a structure of a lithium air battery 20 according to another embodiment.

Referring to FIG. 2, the lithium air battery 20 includes a first current collector 11, a second current collector 12, a cathode 13, an anode 14, a lithium ion-conductive layer 24 between the cathode 13 and the anode 14, an electrolyte 25 including a compound of Formula 1 as described above (hereinafter, referred to as a first electrolyte) between the cathode 13 and the lithium ion conductive layer 24, and a second electrolyte 26 between the anode 14 and the lithium ion-conductive layer 24.

In FIG. 2, the anode 14, the second electrolyte 26, and the lithium ion-conductive layer 24 may be collectively called a protected anode. The cathode 13, the anode 14, and the first electrolyte 25 in FIG. 2 correspond to the cathode 13, the anode 14, and the first electrolyte 15 in FIG. 1, respectively, and thus detailed descriptions thereof will be omitted here.

The lithium ion-conductive layer 24 having lithium-ion conductivity may include an ion-conductive inorganic particle.

The second electrolyte 26 may be, but not limited to, a solid polymer electrolyte or an inorganic solid electrolyte. The second electrolyte 26 may be a lithium ion-conductive solid electrolyte membrane.

The lithium ion-conductive solid electrolyte may be a glass-ceramic solid electrolyte, or a laminated structure of a glass-ceramic solid electrolyte and a solid polymer electrolyte. A "glass-ceramic" refers to a polycrystalline material generated through controlled crystallization of base glass. The lithium ion-conductive solid electrolyte membrane will now be described in greater detail.

The lithium ion-conductive solid electrolyte may include an inorganic material including lithium ion-conductive glass, a lithium ion-conductive crystal (ceramic or glass-ceramic), or a combination thereof. For example, the lithium ion-conductive solid electrolyte membrane may include an oxide, in consideration of chemical stability.

When the lithium ion-conductive solid electrolyte includes a large amount of lithium ion-conductive crystals, a high ionic conductivity may be attainable. For example, the lithium ion-conductive solid electrolyte membrane may include about 50 weight percent (wt %) or greater, about 60 wt % or greater, or about 70 wt % or greater of lithium ion-conductive crystals, based on the total weight of the lithium ion-conductive solid electrolyte membrane.

The lithium ion-conductive crystals may be lithium ion-conductive particles having a Perovskite structure, such as $Li_3N$, LISICON, $La_{0.55}Li_{0.35}TiO_3$, and the like, $LiTi_2P_3O_{12}$ crystals having a NASICON structure, or a glass-ceramic able to precipitate these crystals.

For example, the lithium ion-conductive crystals may be $Li_{1+x+y}(Al, Ga)_x(Ti, Ge)_{2-x}Si_yP_{3-y}O_{12}$, wherein $0 \leq x \leq 1$ and $0 \leq y \leq 1$, for example, $0 \leq x \leq 0.4$ and $0 \leq y \leq 0.6$, or $0.1 \leq x \leq 0.3$ and $0.1 \leq 0 \leq y \leq 0.4$. Crystals that do not include grain boundaries impairing conduction of ions may be advantageous in terms of conductivity. For example, a glass-ceramic substantially free of pores or grain boundaries that impair conduction of ions may have high ionic conductivity and high chemical stability.

Non-limiting examples of the lithium ion-conductive glass-ceramic include lithium-aluminum-germanium-phosphate (LAGP), lithium-aluminum-titanium-phosphate (LATP), and lithium-aluminum-titanium-siliconphosphate (LATSP).

For example, when a parent glass with a composition of $Li_2O$—$Al_2O_3$—$TiO_2$—$SiO_2$—$P_2O_5$ is thermally treated for crystallization, a main crystal phase of $Li_{1+x+y}Al_xTi_{2-x}Si_yP_{3-y}O_{12}$, wherein $0 \leq x \leq 1$ and $0 \leq y \leq 1$, may be obtained. For example, $0 \leq x \leq 0.4$ and $0 \leq y \leq 0.6$, and in some embodiments, $0.1 \leq x \leq 0.3$ and $0.1 \leq y \leq 0.4$.

As used herein, the pores or grain boundaries blocking conduction of ions refer to a structure that lowers the lithium ion conductivity of the entire inorganic material including lithium ion-conductive crystals to 1/10 or less of the lithium ion conductivity of the lithium ion-conductive crystals of the inorganic material.

The terms "glass-ceramic" refers to a material obtained by thermally treating glass to precipitate crystalline phases from glass phases in the glass, the glass-ceramic including amorphous solid and crystals. The glass-ceramic may also refer to a material completely phase-transitioned from glass phases to crystalline phases, for example, a material with a 100% by weight degree of crystallization. In some embodiments the glass-ceramic may include a material having a 100% by weight degree of crystallization. The glass-ceramic includes nearly zero pores among crystal particles or in a crystal even when crystallized 100% by weight.

Since the lithium ion-conductive solid electrolyte includes a large amount of glass-ceramic, a high ionic conductivity may be obtained. The lithium ion-conductive solid electrolyte may include glass-ceramic at about 80 wt % or greater, and in some embodiments, about 85 wt % or greater, or about 90 wt % or greater, based on the total weight of lithium ion-conductive solid electrolyte, to obtain high ionic conductivities.

A $Li_2O$ component in the glass-ceramic may serve as a $Li^+$ ion carrier and is an effective component for lithium-ion conductivity. To easily obtain a high ionic conductivity, the amount of the $Li_2O$ component may be about 12 mole % to about 18 mole %, and in some embodiments, about 13 mole % to about 17 mole %, and in some other embodiments, about 14 mole % to about 16 mole %, based on the total number of moles in the glass-ceramic. When the amount of the $Li_2O$ component is within any of these ranges, the thermal stability of the glass-ceramic may not be reduced and the conductivity of the glass-ceramic may also be improved.

An $Al_2O_3$ component in the glass-ceramic may improve the thermal stability of the parent glass and may improve lithium-ion conductivity by being present as $Al^{3+}$ ions in a crystal phase. To facilitate these effects, the amount of the $Al_2O_3$ component may be about 5 to about 10 mole %, and in some embodiments, about 5.5 to about 9.5 mole %, and in some other embodiments, about 6 to 9 mole %, based on the total number of moles in the glass-ceramic. When the amount of the $Al_2O_3$ component is within any of these ranges, the thermal stability of the glass-ceramic may not be deteriorated and the conductivity of the glass-ceramic may be improved.

A $TiO_2$ component in the glass-ceramic as a component in the crystal phase is an effective component involved in the formation of glass and the crystal phase. To facilitate glass formation and precipitate a main crystal phase thereof on the glass to obtain a higher ionic conductivity, the amount of the $TiO_2$ component may be about 35 to about 45 mole %, and in some embodiments, about 36 to 43 mole %, and in some other embodiments, about 37 to about 42 mole %, based on the total number of moles in the glass-ceramic. When the amount of the $TiO_2$ component is within any of these ranges, the thermal stability of the glass-ceramic may not be deteriorated and the conductivity of the glass-ceramic may be improved.

A $SiO_2$ component in the glass-ceramic may improve the melting properties and thermal stability of the parent glass and may improve lithium-ion conductivity by being present as $Si^{4+}$ ions in the crystal phase. To facilitate these effects, the amount of the $SiO_2$ component may be about 1 to about 10 mole %, and in some embodiments, about 2 to about 8 mole %, and in some other embodiments, about 3 to about 7 mole %, based on the total number of moles in the glass-ceramic. When the amount of the $SiO_2$ component is within any of these ranges, the thermal stability of the glass-ceramic may not be deteriorated and the conductivity of the glass-ceramic may be improved.

A $P_2O_5$ component in the glass-ceramic, as a component in a crystal phase, is an effective component involved in the formation of glass and the crystal phase. The amount of the $P_2O_5$ component may be about 30 to about 40 mole %, and in some embodiments, about 32 to about 39 mole %, and in some other embodiments, about 33 to about 38 mole %, based on the total number of moles in the glass-ceramic. When the amount of the $P_2O_5$ component is within any of these embodiments, the glass-ceramic may have improved characteristics without precipitation of the crystal phase from the glass phase.

When the glass-ceramic has any of the above-described compositions, glass may be easily formed by casting molten glass, and the glass-ceramic in the crystal phase obtained by thermally treating the glass may have a high lithium-ion conductivity of about $1 \times 10^{-3}$ Siemens per centimeter ($S \cdot cm^{-1}$).

When a glass-ceramic having a different, but similar crystalline structure as above, is used, the $Al_2O_3$ component and the $TiO_2$ component may be partially or fully substituted with a $Ga_2O_3$ component and a $GeO_2$ component, respectively. In some other embodiments, to lower a melting point of the glass-ceramic or improve the stability of glass, a trace of an additional material may be used in a range of amounts that do not significantly deteriorate ionic conductivity.

The lithium ion-conductive solid electrolyte may further include a solid polymer electrolyte, in addition to the glass-ceramic. For example, the solid polymer electrolyte may be a polyethylene oxide doped with a lithium salt. Non-limiting examples of the lithium salt are $LiN(SO_2CF_2CF_3)_2$, $LiBF_4$, $LiPF_6$, $LiSbF_6$, $LiAsF_6$, $LiClO_4$, $LiCF_3SO_3$, $LiN(SO_2CF_3)_2$, $LiN(SO_2C_2F_5)_2$, $LiC(SO_2CF_3)_3$, $LiN(SO_3CF_3)_2$, $LiC_4F_9SO_3$, and $LiAlCl_4$.

The solid polymer electrolyte may form a laminated structure with the glass-ceramic. The glass-ceramic may be disposed between a first solid polymer electrolyte and a second solid polymer electrolyte that each independently includes a component of the above-listed components.

The lithium ion-conductive solid electrolyte may be used as a single layer or a plurality of layers.

The operation principle of the lithium air batteries 10 and 20 according to embodiments of the present disclosure are as follows. During discharging, lithium ions from the anode 14 produce a lithium oxide by reaction with oxygen from the cathode 13, through the reduction of the oxygen (oxygen reduction reaction: ORR). On the other hand, during charging, the lithium oxide is reduced, while oxygen is produced by oxygen evolution reaction (OER).

When the electrolyte is a nonaqueous electrolyte, the reaction mechanism may be represented by Reaction Scheme 1.

$4Li + O_2 \leftrightarrow 2Li_2O$  $E° = 2.91V$, $2Li + O_2 \leftrightarrow Li_2O_2$  $E° = 3.10V$.    Reaction Scheme 1

When the electrolyte is an aqueous electrolyte, the reaction mechanism may be represented by Reaction Scheme 2.

$4Li + O_2 + 2H_2O \leftrightarrow 4LiOH$  $E° = 3.45V$.    Reaction Scheme 2

As used herein, the term "air" is not limited to atmospheric air, and for convenience, may refer to a combination of gases including oxygen, or pure oxygen gas. This broad definition of "air" also applies to other terms, including "air battery" and "air electrode".

The lithium air battery is available either as a lithium primary battery or a lithium secondary battery. The lithium air battery may have any of various shapes, and in some embodiments, may have a shape like a coin, a button, a sheet, a stack, a cylinder, a plane, or a horn. The lithium air battery may be applicable as a large battery for electric vehicles.

Substituents in the formulas above may be defined as follows.

As used herein, the term "alkyl group" indicates a completely saturated, branched or unbranched (or a straight or linear) hydrocarbon group.

Non-limiting examples of the alkyl group include a methyl group, an ethyl group, a n-propyl group, an isopropyl group, a n-butyl group, an isobutyl group, a sec-butyl group, a t-butyl group, an isopentyl group, a neopentyl group, an iso-amyl group, a n-hexyl group, a 3-methylhexyl group, a 2,2-dimethylpentyl group, a 2,3-dimethylpentyl group, and a n-heptyl group.

At least one hydrogen atom of the alkyl group may be substituted with a halogen atom, a $C_1$-$C_{20}$ alkyl group substituted with a halogen atom (for example, $CCF_3$, $CHCF_2$, $CH_2F$, $CCl_3$, and the like), a $C_1$-$C_{20}$ alkoxy group, a $C_2$-$C_{20}$ alkoxyalkyl group, a hydroxyl group, a nitro group, a cyano group, an amino group, an alkyl amino group, an amidino group, a hydrazine, a hydrazone, a carboxyl group or a salt thereof, a sulfonyl group, a sulfamoyl group, a sulfonic acid group or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, a $C_6$-$C_{20}$ heteroaryloxyalkyl group, or a $C_6$-$C_{20}$ heteroarylalkyl group.

The term "halogen atom" indicates fluorine, bromine, chloride, iodine, and the like.

As used herein, the term "alkoxy group" represents "alkyl-O—", wherein the alkyl group is the same as described above.

Non-limiting examples of the alkoxy group include a methoxy group, an ethoxy group, an n-propoxy group, a 2-propoxy group, an n-butoxy group, a t-butoxy group, an n-pentyloxy group, an n-hexyloxy group, a cyclopropoxy group, and a cyclohexyloxy group.

At least one hydrogen atom in the alkoxy group may be substituted with one of the same substituents as described above in conjunction with the above-described alkyl group.

The unsubstituted alkenyl group indicates an unsaturated alkyl group having at least one carbon-carbon double bond in the center or at a terminal of the unsubstituted alkyl group.

Non-limiting examples of the alkenyl group include an ethenyl group, a propenyl group, a butenyl group, and the like.

At least one hydrogen atom in the unsubstituted alkenyl group may be substituted with one of the same substituents as described above in conjunction with the substituted alkyl group.

The unsubstituted alkynyl group indicates an alkyl group having at least one carbon-carbon triple bond in the center or at a terminal of the above-described alkyl group.

Non-limiting examples of the unsubstituted alkynyl group include an acetylene group, a propylene group, an isopropylacetylene group, a t-butylacetylene group.

At least one hydrogen atom in the alkynyl group may be substituted with one of the same substituents as described above in conjunction with the substituted alkyl group. Non-limiting examples of a substituted alkynyl group include a phenylacetylene group, a naphthylacetylene group, and a diphenylacetylene group.

As used herein, the term "aryl" group, which is used alone or in combination, refers to an aromatic hydrocarbon containing at least one ring.

The term "aryl" group is construed as including a group with an aromatic ring fused to at least one cycloalkyl ring.

Non-limiting examples of the aryl group include a phenyl group, a naphthyl group, and a tetrahydronaphthyl group.

At least one hydrogen atom in the aryl group may be substituted with one of the same substituents as described above in connection with the alkyl group.

As used herein, the term "heteroaryl group" indicates a monocyclic or bicyclic organic compound including at least one heteroatom selected from among nitrogen (N), oxygen (O), phosphorous (P), and sulfur (S), wherein the rest of the cyclic atoms are all carbon. The heteroaryl group may include, for example, one to five heteroatoms, and in some embodiments, may include a five- to ten-membered ring.

In the heteroaryl group, S or N may be present in various oxidized forms.

Non-limiting examples of the monocyclic heteroaryl group include a thienyl group, a furyl group, a pyrrolyl group, an imidazolyl group, a pyrazolyl group, a thiazolyl group, an isothiazolyl group, a 1,2,3-oxadiazolyl group, a 1,2,4-oxadiazolyl group, a 1,2,5-oxadiazolyl group, a 1,3,4-oxadiaxolyl group, a 1,2,3-thiadiazolyl group, a 1,2,4-thiadiazolyl group, a 1,2,5-thiadiazolyl group, a 1,3,4-thiadiazolyl group, an isothiazol-3-yl group, an isothiazol-4-yl group, an isothiazol-5-yl group, an oxazol-2-yl group, an oxazol-4-yl group, an oxazol-5-yl group, an isoxazol-3-yl group, an isoxazol-4-yl group, an isoxazol-5-yl group, a 1,2,4-triazol-3-yl group, a 1,2,4-triazol-5-yl group, a 1,2,3-triazol-4-yl group, a 1,2,3-triazol-5-yl group, a tetrazolyl group, a pyrid-2-yl group, a pyrid-3-yl group, a 2-pyrazin-2-yl group, a pyrazin-4-yl group, a pyrazin-5-yl group, a 2-pyrimidin-2-yl group, a 4-pyrimidin-2-yl group, or a 5-pyrimidin-2-yl group.

The term "heteroaryl" group includes a heteroaromatic ring fused to at least one of an aryl group, a cycloaliphatic group, or a heterocyclic group.

Non-limiting examples of the bicyclic heteroaryl group include an indolyl group, an isoindolyl group, an indazolyl group, an indolizinyl group, a purinyl group, a quinolizinyl group, a quinolinyl group, and an isoquinolinyl group. At least one hydrogen atom of the heteroaryl group may be substituted with one of the same substituents as described above in conjunction with the alkyl group.

The term "sulfonyl" group refers to R"—SO$_2$—, wherein R" may be a hydrogen, an alkyl group, an aryl group, a heteroaryl group, an aryl-alkyl group, a heteroaryl-alkyl group, an alkoxy group, an aryloxy group, a cycloalkyl group, or a heterocyclic group.

The term "sulfamoyl" group may include H$_2$NS(O$_2$)—, an alkyl group-NHS(O$_2$)—, an (alkyl group)$_2$NS(O$_2$)-aryl group-NHS(O$_2$)—, an alkyl group-(aryl group)-NS(O$_2$)—, an (aryl group)$_2$NS(O)$_2$, a heteroaryl group —NHS(O$_2$)—, an (aryl group-alkyl group)-NHS(O$_2$)—, or a (heteroaryl group-alkyl group)-NHS(O$_2$)—.

At least one hydrogen atom of the sulfamoyl group may be substituted with one of the same substituents as described above in conjunction with the alkyl group.

The term "amino group" refers to a group with a nitrogen atom covalently bonded to at least one carbon or heteroatom.

The amino group may include, for example, —NH$_2$ and substituted moieties.

The term "amino group" also comprises an "alkylamino group" with nitrogen bound to at least one additional alkyl group, and "arylamino" and "diarylamino" groups with at least one or two nitrogen atoms bound to an independently selected aryl group.

The term "carbon ring" refers to a cyclic group having 5 to 10 carbon atoms, such as a cyclohexyl group. At least one hydrogen atom in the carbon ring may be substituted with one of the same substituents as described above in connection with the alkyl group.

At least one hydrogen atom in the alkoxycarbonyl group, arylcarbonyl group, and heteroarylcarbonyl group may be substituted with one of the same substituents as described above in connection with the alkyl group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted C1-C30 alkyl" refers to a C1-C30 alkyl group substituted with C6-C30 aryl group, the total number of carbon atoms in the resulting aryl substituted alkyl group is C7-C60.

One or more embodiments of the present disclosure will now be described in detail with reference to the following examples. However, these examples are only for illustrative purposes and are not intended to limit the scope of the one or more embodiments of the present disclosure.

EXAMPLES

Preparation Example 1

Preparation of Compound of Formula 7a

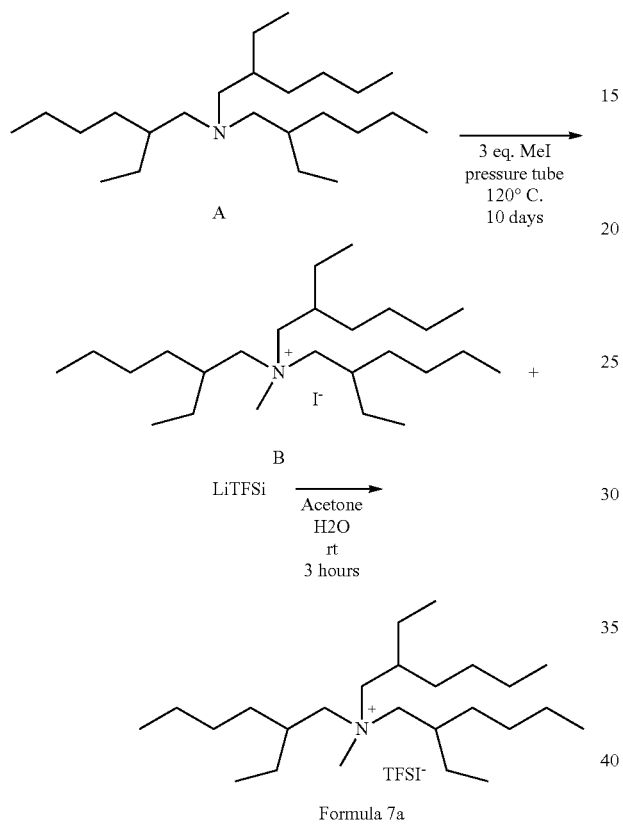

About 1 gram (g) of compound (A) and 3 equivalents of iodomethane were added into a pressure tube and reacted at about 120° C. for about 10 days to obtain compound (B).

About 1.5 equivalents of lithium bis(trifluoromethylsulfonyl)imide (LiTFSI), 10 milliliters (mL) of acetone, and 10 mL of water were added to 1 g of compound (B), and then reacted at about 25° C. for about 3 hours to obtain a compound represented by Formula 7a (EH3).

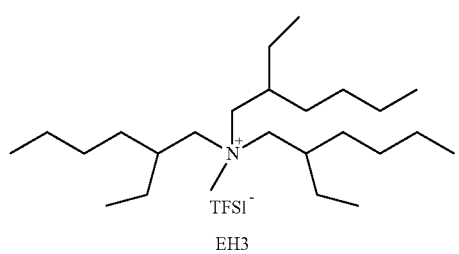

Formula 7a

EH3

Example 1

Preparation of Electrolyte

About 0.15 g of LiTFSI (bis(trifluoromethylsulfonyl)imide) was added to 1 g of the compound of Formula 7a (EH3) to prepare an electrolyte. The amount of the compound of Formula 7a in the electrolyte was about 87 parts by weight based on a total weight of the electrolyte of 100 parts by weight.

Example 2

Preparation of Electrolyte

An electrolyte was prepared in the same manner as in Example 1, except that the amount of the compound of Formula 7a was about 15 parts by weight based on a total weight of the electrolyte of 100 parts by weight.

Example 3

Preparation of Electrolyte

An electrolyte was prepared in the same manner as in Example 1, except that the amount of the compound of Formula 7a was about 97 parts by weight based on a total weight of the electrolyte of 100 parts by weight.

Example 4

Preparation of Electrolyte

An electrolyte was prepared in the same manner as in Example 1, except that a compound represented by Formula 8a, instead of the compound of Formula 7a, was used.

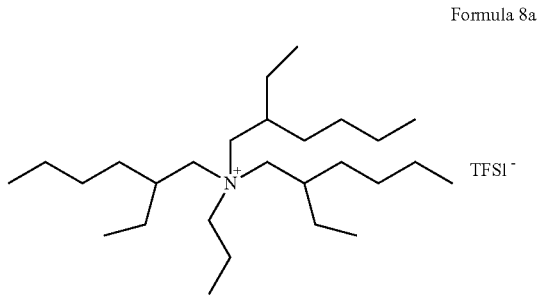

Formula 8a

Example 5

Preparation of Electrolyte

An electrolyte was prepared in the same manner as in Example 1, except that a compound represented by Formula 9a, instead of the compound of Formula 7a, was used.

Formula 9a

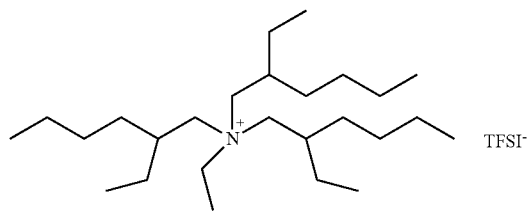
TFSI⁻

Example 6

Preparation of Electrolyte

An electrolyte was prepared in the same manner as in Example 1, except that a compound represented by Formula 10a, instead of the compound of Formula 7a, was used.

Formula 10a

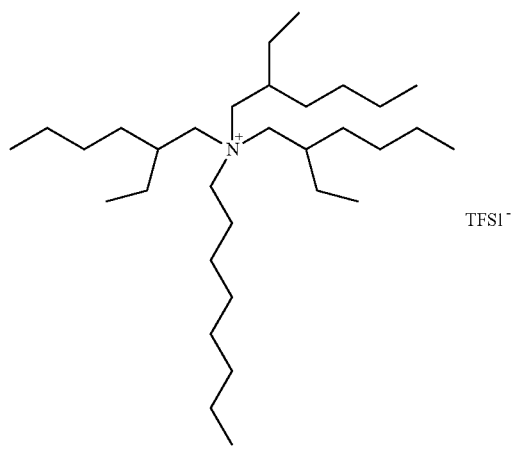
TFSI⁻

Example 7

Preparation of Electrolyte

An electrolyte was prepared in the same manner as in Example 1, except that a compound represented by Formula 11a, instead of the compound of Formula 7a, was used.

Formula 11a

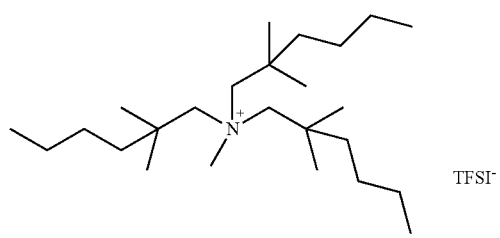
TFSI⁻

Comparative Example 1

Preparation of Electrolyte

About 0.15 g of LiTFSI was added to 1 g of a compound of Formula 12 to prepare an electrolyte. The amount of the compound of Formula 12 in the electrolyte was about 87 parts by weight based on a total weight of the electrolyte of 100 parts by weight.

Formula 12

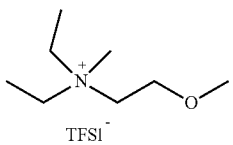
TFSI⁻

Comparative Example 2

Preparation of Electrolyte

About 0.15 g of LiTFSI was added to 1 g of a compound (PP13) of Formula 13 to prepare an electrolyte. The amount of the compound of Formula 13 in the electrolyte was about 87 parts by weight based on a total weight of the electrolyte of 100 parts by weight.

Formula 13

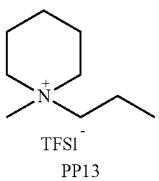
TFSI⁻
PP13

Comparative Example 3

Preparation of Electrolyte

About 0.15 g of LiTFSI was added to 1 g of a compound of Formula 14 to prepare an electrolyte. The amount of the compound of Formula 14 in the electrolyte was about 87 parts by weight based on a total weight of the electrolyte of 100 parts by weight.

Formula 14

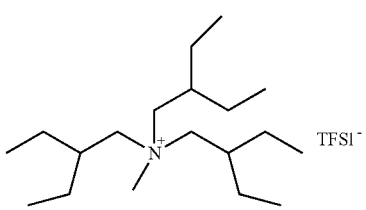
TFSI⁻

Comparative Example 4

Preparation of Electrolyte

About 0.15 g of LiTFSI was added to 1 g of a compound of Formula 15 to prepare an electrolyte. The amount of the compound of Formula 15 in the electrolyte was about 87 parts by weight based on a total weight of the electrolyte.

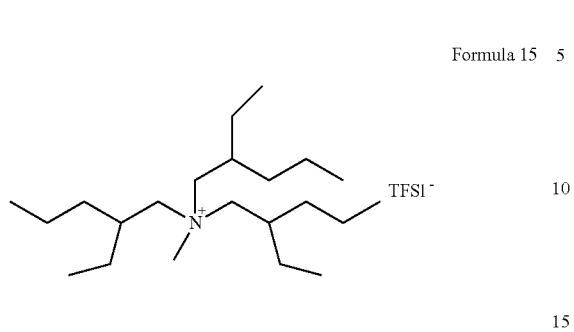

Formula 15

Comparative Example 5

Preparation of Electrolyte

About 0.15 g of LiTFSI was added to 1 g of a compound of Formula 16 to prepare an electrolyte. The amount of the compound of Formula 16 in the electrolyte was about 87 parts by weight based on a total weight of the electrolyte of 100 parts by weight.

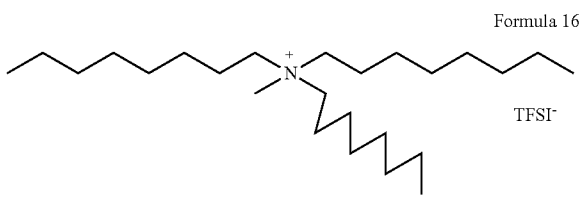

Formula 16

Comparative Example 6

Preparation of Electrolyte

About 0.15 g of LiTFSI was added to 1 g of a compound of Formula 17 to prepare an electrolyte. The amount of the compound of Formula 17 in the electrolyte was about 87 parts by weight based on a total weight of the electrolyte.

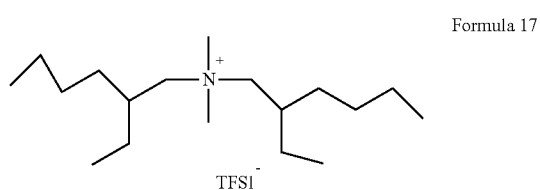

Formula 17

Comparative Example 7

Preparation of Electrolyte

About 0.15 g of LiTFSI was added to 1 g of a compound of Formula 18 to prepare an electrolyte. The amount of the compound of Formula 18 in the electrolyte was about 87 parts by weight based on a total weight of the electrolyte of 100 parts by weight.

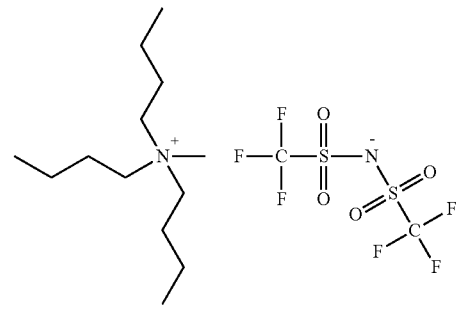

Formula 18

Example 8

Manufacture of Lithium Air Battery 40 parts by weight of carbon (Super-P), 10 parts by weight of polytetrafluoroethylene (PTFE), and 50 parts by weight of N-methylpyrrolidone (NMP) were mixed to prepare a cathode slurry, which was then coated and roll-pressed to prepare a cathode sheet. The cathode sheet was pressed to adhere to a stainless mesh, and then vacuum dried in an oven at 100° C. for 120 minutes to obtain a cathode.

A hole was punched in the center of a 5 centimeter (cm) by 5 cm-sized polypropylene-coated aluminum film (having a thickness of 200 micrometers (μm)), and was then blocked with a film of $Li_{1+x+y}Al_xTi_{2-x}Si_yP_{3-y}O_{12}$ (LATP), wherein $0 \leq x \leq 2$ and $0 \leq y \leq 3$, (having a thickness of about 150 μm, available from Ohara corporation), by using an adhesive, thereby forming a first aluminum film including an LATP region. Next, a second aluminum film having a size of 5 cm×5 cm, a copper current collector (having a thickness of about 20 μm), a lithium foil (1.4 cm×1.4 cm, having a thickness of about 100 μm), a polypropylene-based Celgard-3501 separator (having a thickness of 25 μm, available from Celgard) impregnated with the electrolyte solution (including 1M LiTFSI) of Example 1, and the first aluminum film were sequentially stacked upon one another, and then heated in a vacuum to bind together, thereby obtaining a protected lithium anode that is enclosed in the aluminum pouch.

The protected lithium anode was mounted in a side of a stainless case, and the cathode with a polypropylene separator (Celgard-3501, available from Celgard) having a thickness of 25 μm was mounted in the side of the stainless case opposite to the anode. Next, after the electrolyte of Example 1 was injected between the cathode and the anode, a porous gas diffusion layer made of carbon fiber, and a foamed nickel plate were sequentially disposed on the cathode, and a pressing member that allows air to reach the cathode was attached to fix a cell, thereby completing the manufacture of a lithium air battery.

Examples 9 to 14

Manufacture of Lithium Air Batteries

Lithium air batteries were manufactured in the same manner as in Example 8, except that the electrolytes of Examples 2 to 7, instead of the electrolyte of Example 1, were used, respectively.

Comparative Examples 8 to 14

Manufacture of Lithium Air Batteries

Lithium air batteries were manufactured in the same manner as in Example 8, except that the electrolytes of Comparative Examples 1 to 7, instead of the electrolyte of Example 1, were used, respectively.

Evaluation Example 1

Stability Evaluation ($^1$H-NMR, Mass Spectrometry, $^{19}$F-NMR)

The lithium air batteries of Example 8 and Comparative Example 8 were discharged in a chamber at 1 atmosphere of oxygen at about 60° C. with a constant current of about 0.2 mA/cm$^2$ to a voltage of about 2 V (with respect to Li) and charging with the same current to about 4.0 V. This charge-discharge cycle was repeated 52 times in total.

After the charge-discharge cycles, the anode was quenched with deuterium oxide (D$_2$O), and a solution used in the quenching was collected and analyzed by $^1$H-NMR using a BRUKER 300 MHz NMR spectrometer.

Figure 4:
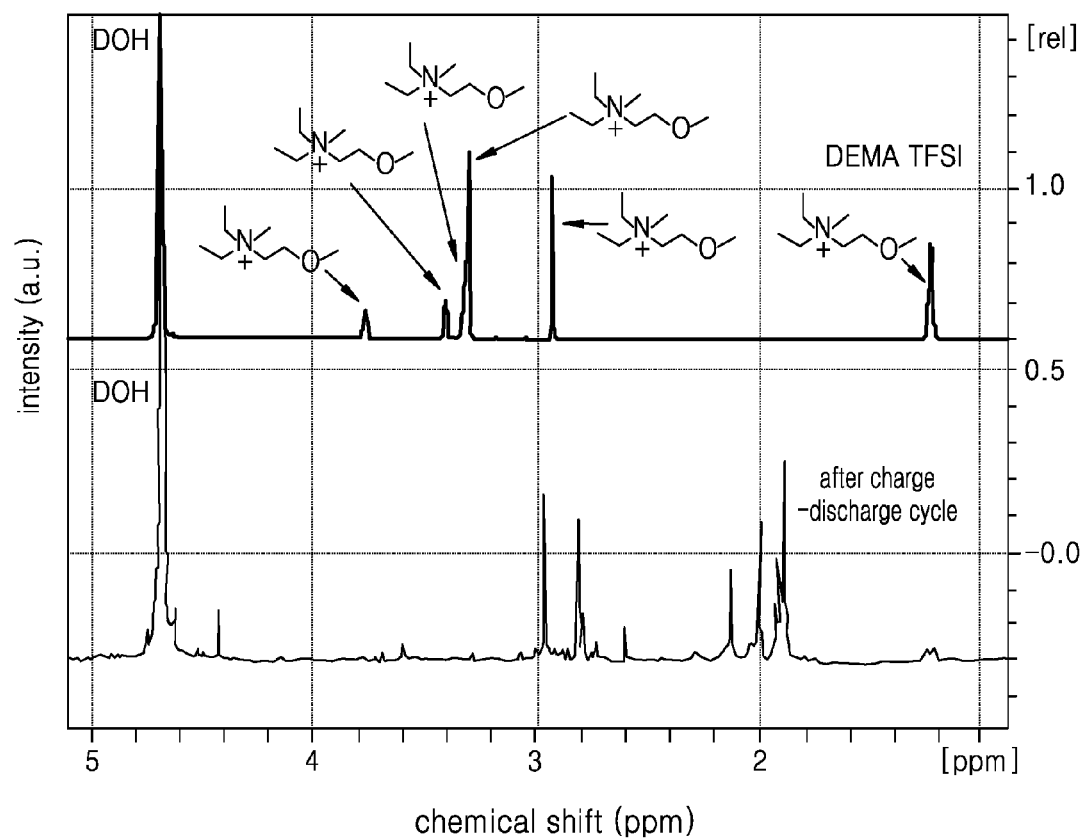
FIG. 4 illustrates an $^1$H-NMR spectrum plot of intensity (arbitrary units, a.u.) versus chemical shift (parts per million, ppm) relative to tetramethylsilane of a compound represented by Formula 12 used in a lithium air battery of Comparative Example 8 before and after a charge-discharge cycle.

The resulting NMR spectra (of the lithium air battery of Comparative Example 8) before and after the charge-discharge cycle are shown in upper and lower regions in FIG. 4, respectively. The mass spectra of the lithium air battery of Comparative Example 8 before and after the charge-discharge cycle are shown in FIGS. 5A and 5B, respectively.

Referring to FIG. 4, the NMR spectra of the compound represented by Formula 12 in the lithium air battery of Comparative Example 8 were different before and after the charge-discharge cycle, indicating that significant decomposition of cations occurred in the compound represented by Formula 12 of Comparative Example 8 after the charge-discharge cycle.

Figure 5A:
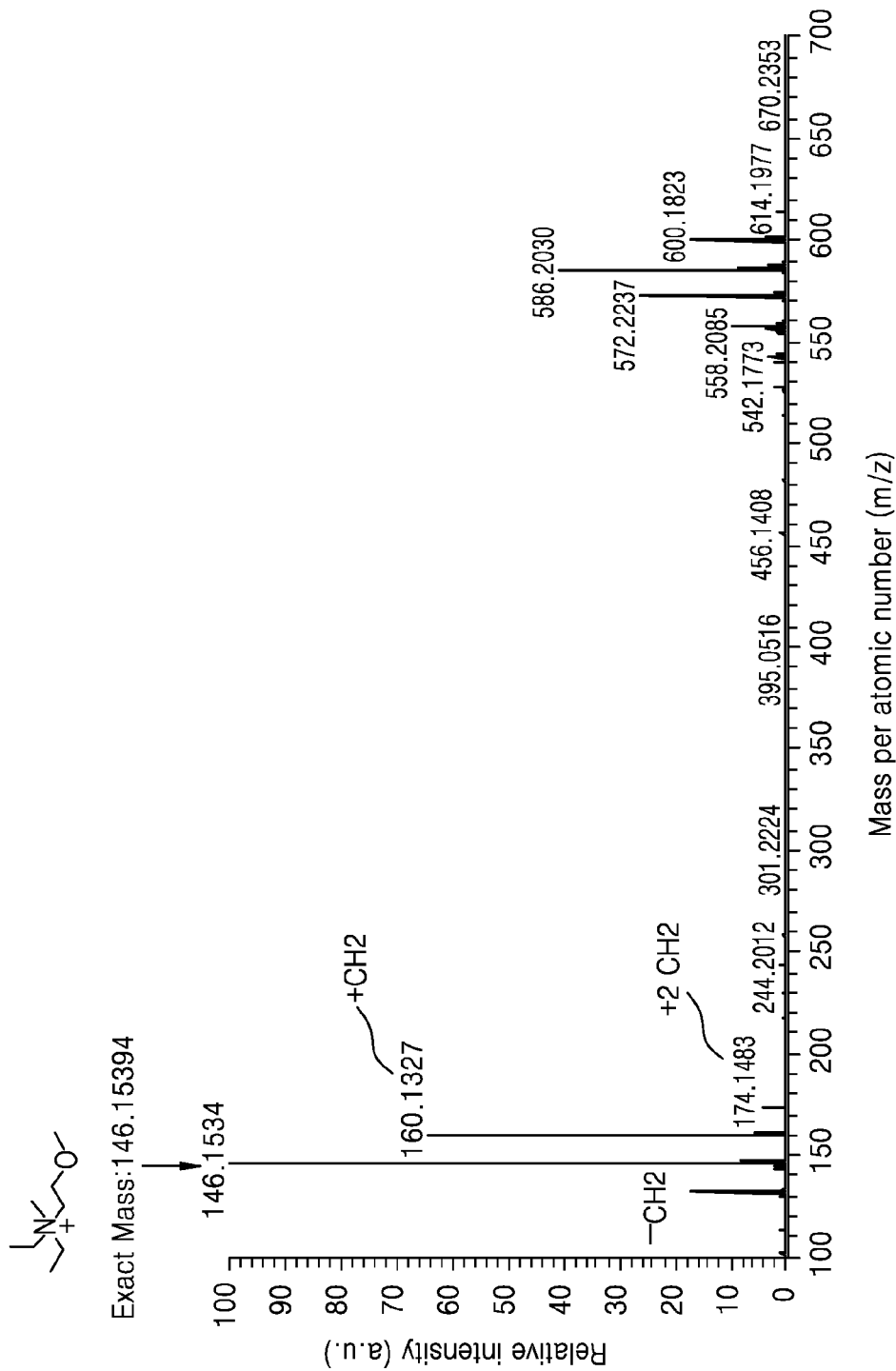
FIGS. 5A and 5B are mass spectra plots of intensity in arbitrary units (a.u.) versus mass (mass per atomic number, m/z) of the compound represented by Formula 12 in the lithium air battery of Comparative Example 8 before and after the charge-discharge cycle, respectively.
Figure 5B:
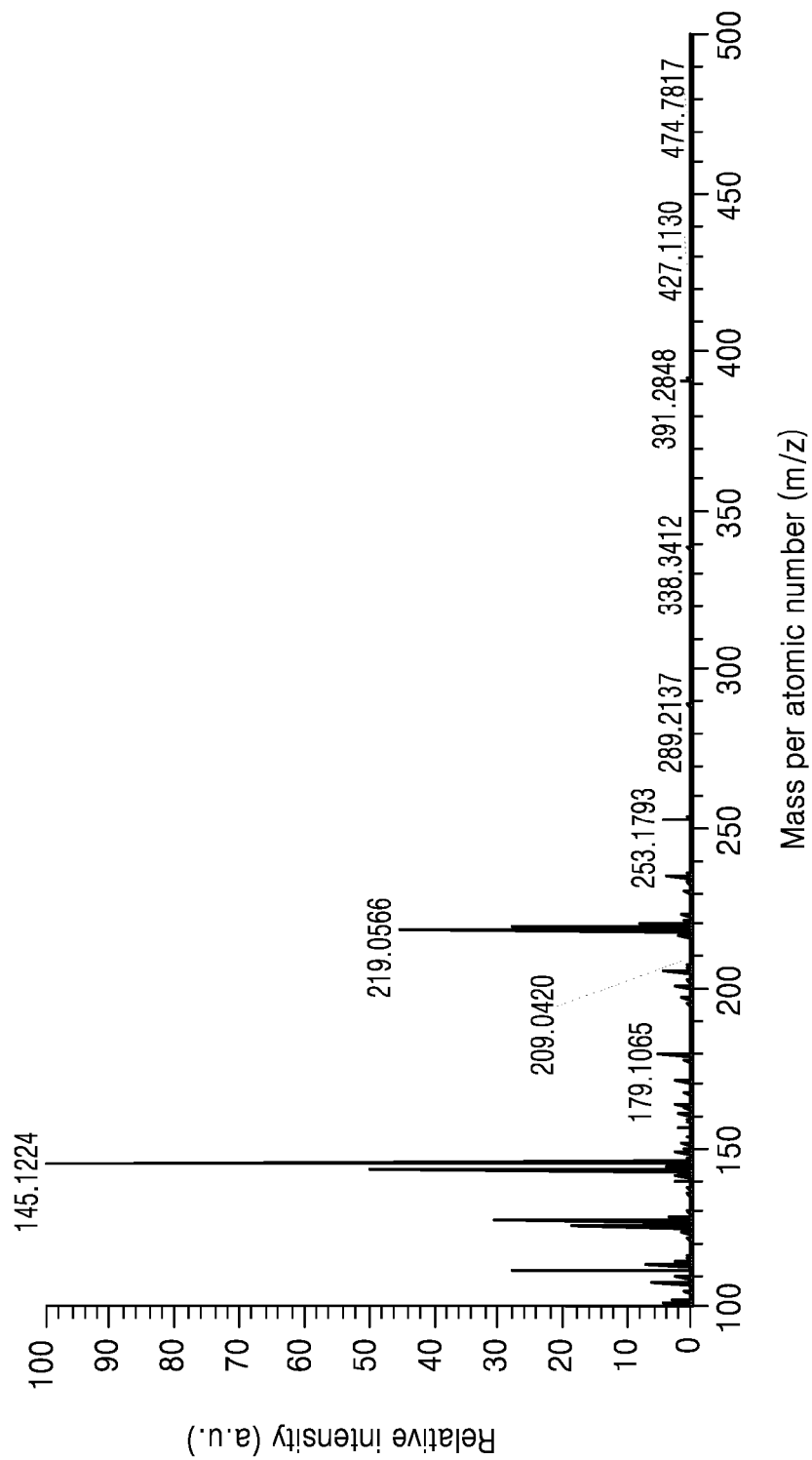

Referring to FIGS. 5A and 5B, an identified material from the lithium air battery of Comparative Example 8 after the charge-discharge cycle had a mass-to-charge ratio (m/z) of about 219.07 Daltons (Da), which means that no peak with a mass corresponding to the mass of the compound represented by Formula 12 (was found in the mass spectra obtained after the charge-discharge cycle. This result indicates that the compound represented by Formula 12 was decomposed after the charge-discharge cycle.

Figure 3A:
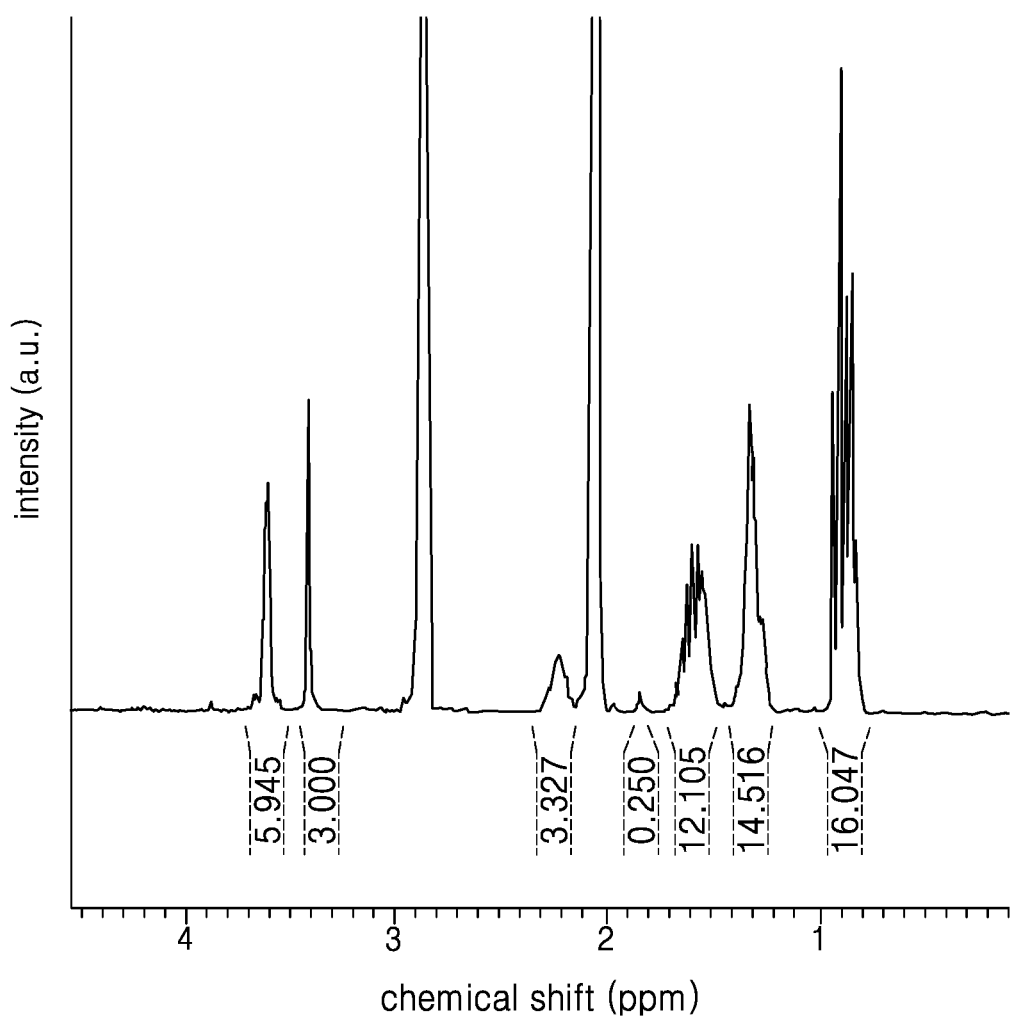
FIGS. 3A and 3B are proton nuclear magnetic resonance ($^1$H-NMR) spectra plots of intensity (arbitrary units, a.u.) versus chemical shift (parts per million, ppm) relative to tetramethylsilane of a compound represented by Formula 7a used in a lithium air battery of Example 8 before and after a charge-discharge cycle, respectively.
Figure 3B:
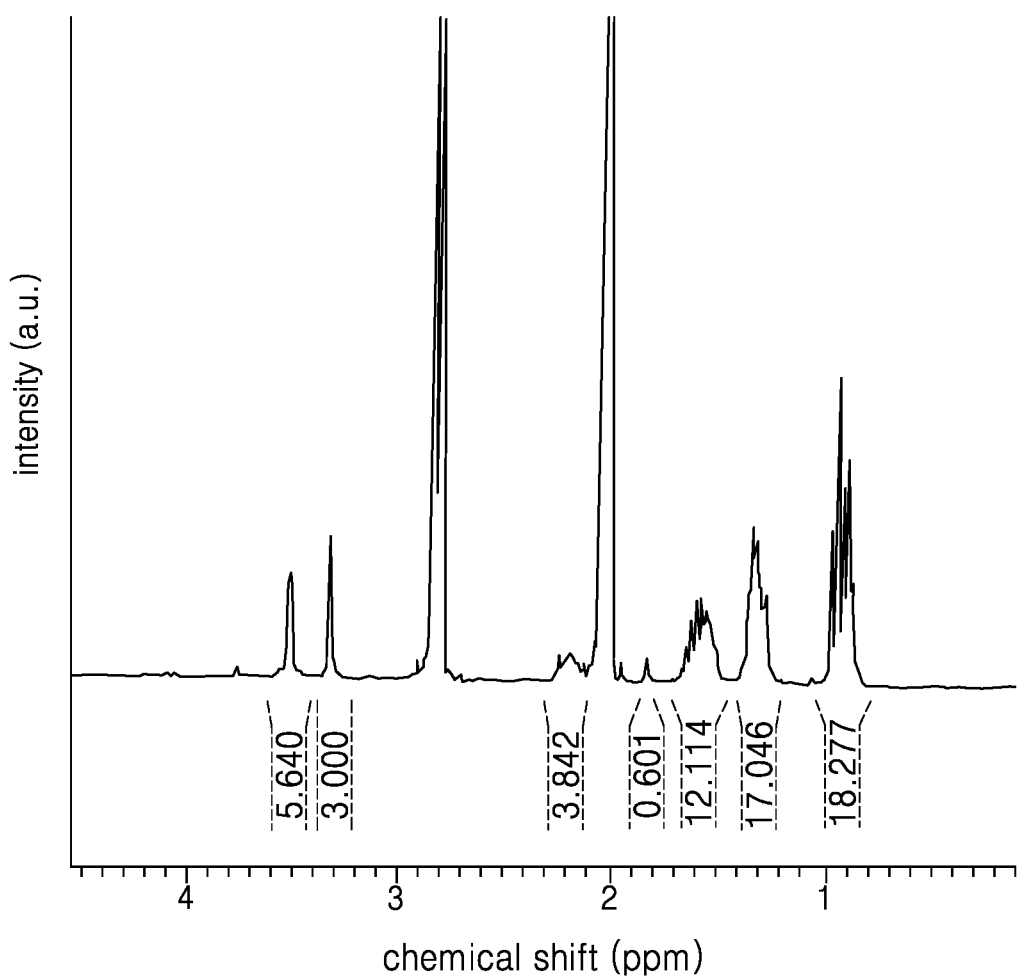

The $^1$H-NMR spectra of the lithium air battery of Example 8 before and after the charge-discharge cycle are shown in FIGS. 3A and 3B, respectively. Referring to FIGS. 3A and 3B, $^1$H-NMR peaks corresponding to those of the cationic portion of the compound represented by Formula 7a were detected both before and after the charge-discharge cycle. Peaks corresponding to the cationic portion of Formula 7a were also found in the mass spectra of the lithium air battery of Example 8 before and after the charge-discharge cycle. The results indicate that the compound represented by Formula 7a included in the electrolyte of the lithium air battery of Example 8 has improved stability of the cationic portion.

The lithium air battery of Example 8 was also analyzed before and after the charge-discharge cycle by $^{19}$F-NMR using a BRUKER 300 MHz NMR spectrometer. The results are shown in FIG. 5C.

Figure 5C:
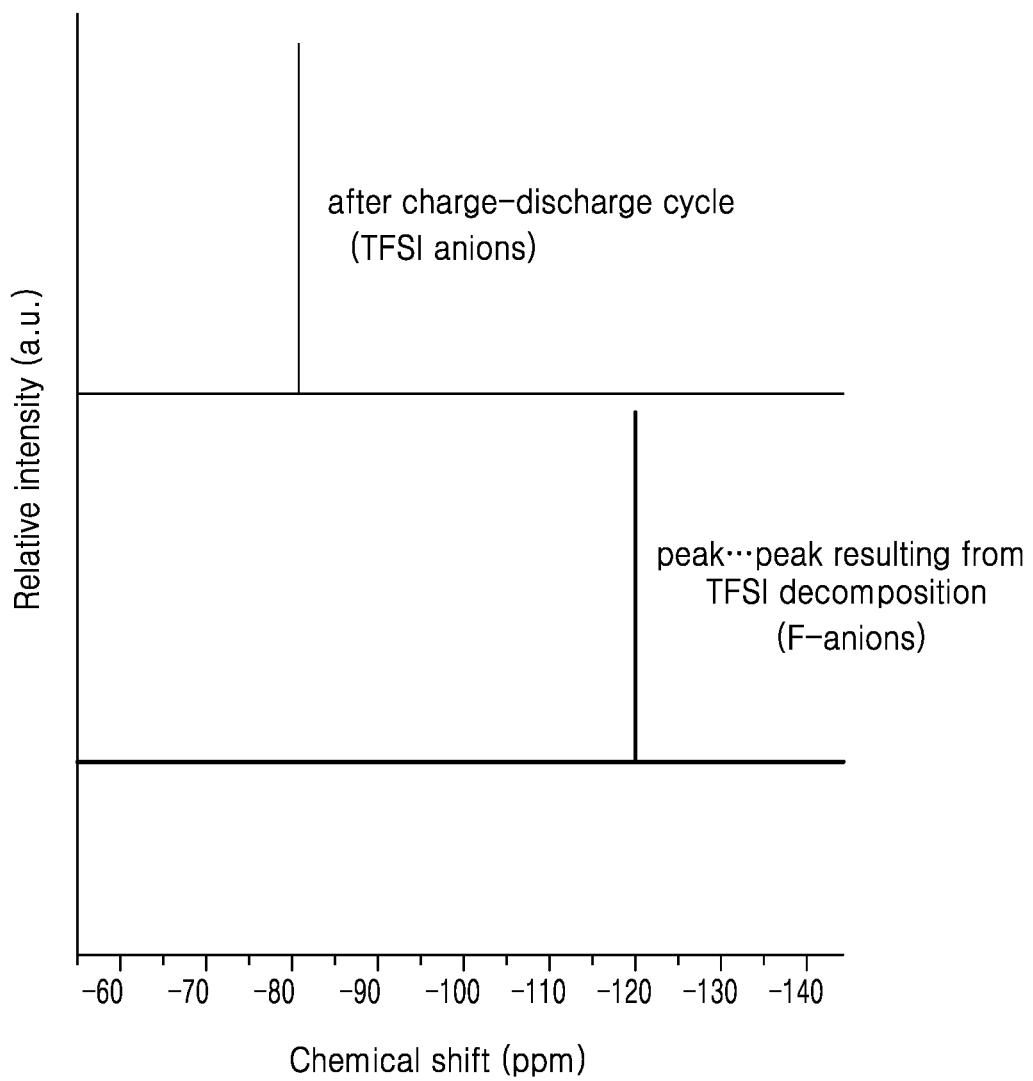
FIG. 5C illustrates an $^{19}$F-NMR spectrum plot of intensity (arbitrary units, a.u.) versus chemical shift (parts per million, ppm) relative to $CFCl_3$ of the compound represented by Formula 12 used in the lithium air battery of Example 8 before and after the charge-discharge cycle.

The decomposition of anions in an ionic liquid before or after a charge-discharge cycle may lead to generation of F anions resulting from decomposition of TFSI, as illustrated in a lower region of FIG. 5C. However, as shown in the $^{19}$F-NMR spectra in an upper region of FIG. 5C, no peaks of the F anions appeared before and after the charge-discharge cycle on the lithium air battery of Example 3, indicating that the compound represented by Formula 7a included in the lithium air battery of Example 8 has improved stability of its anionic portion.

Evaluation Example 2

Survival Rate Evaluation

About 0.1 g of each of the compound of Formula 12 used in Comparative Example 1, the compound (PP13) of Formula 13 used in Comparative Example 2, and the compound (EH3) of Formula 7a used in Examples 1, 2, and 3 was added to a 10 weight/volume percent (w/v %) aqueous NaOH solution and then thermally treated at about 80° C. for about 1 day. Each of the sample solutions before the thermal analysis was also analyzed by $^1$H-NMR to evaluate a survival rate of the alkaline sample solution.

Survival rates of sample solutions prepared in the same manner as described above using, instead of the compound (EH3) of Formula 7a used in Example 1, the compounds of Formulas 8a, 9a, 10a, and 11 a used respectively in Examples 4 to 7, and the compounds of Formulas 13 to 18 used respectively in Comparative Examples 2 to 7 were evaluated. The evaluation results of survival rates are shown in Table 1.

TABLE 1

| Example | Survival rate (%) |
|---|---|
| Example 1 (EH3) | 99.7 |
| Example 2 | 99.4 |
| Example 3 | 99.8 |
| Example 4 | 99.2 |
| Example 5 | 98.7 |
| Example 6 | 97.9 |
| Example 7 | 99.1 |
| Comparative Example 1 | 27.5 |
| Comparative Example 2 (PP13) | 67.6 |
| Comparative Example 3 | 78.4 |
| Comparative Example 4 | 81.1 |
| Comparative Example 5 | 52 |
| Comparative Example 6 | 82.5 |
| Comparative Example 7 | 51 |

Referring to Table 1, the compounds of Formulas 7a to 11a used respectively in Examples 1 to 7 were found to have improved survival rate compared to those of the compounds used in Comparative Examples 1 to 7, indicating that the compounds of Formulas 7a, 8a, 9a, 10a, and 11a have improved stability with effectively suppressed decomposition under alkaline conditions, compared to the compounds of Comparative Examples 1 to 7.

Evaluation Example 3

Evaluation of Charge-discharge Characteristics

The lithium air batteries of Example 8 and Comparative Example 8 were discharged in a chamber at 1 atmosphere of oxygen at about 60° C. with a constant current of about 0.2 mA/cm$^2$ to a voltage of about 2 V (with respect to Li) and charging with the same current to about 4.0 V. This charge-discharge cycle was repeated 50 times in total.

Figure 6:
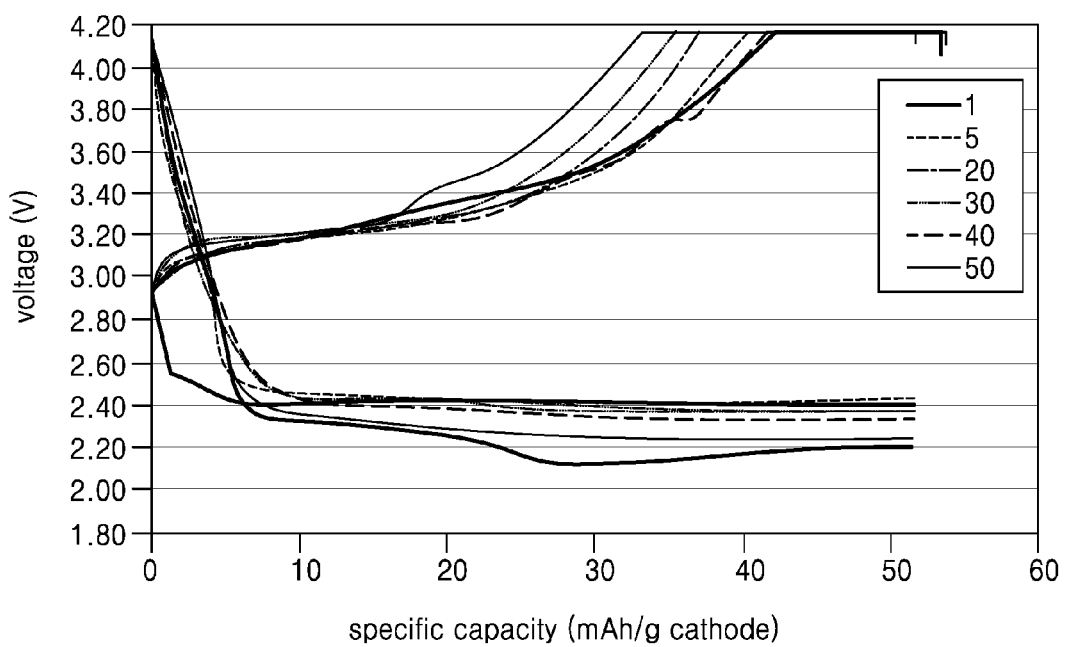
FIGS. 6 and 7 are graphs of voltage in volts (V) versus specific capacity (milliAmpere-hours per gram of cathode, $mAh/g_{cathode}$) which illustrate the results of a charge-discharge test on the lithium air batteries of Example 8 and Comparative Example 8, respectively.
Figure 7:
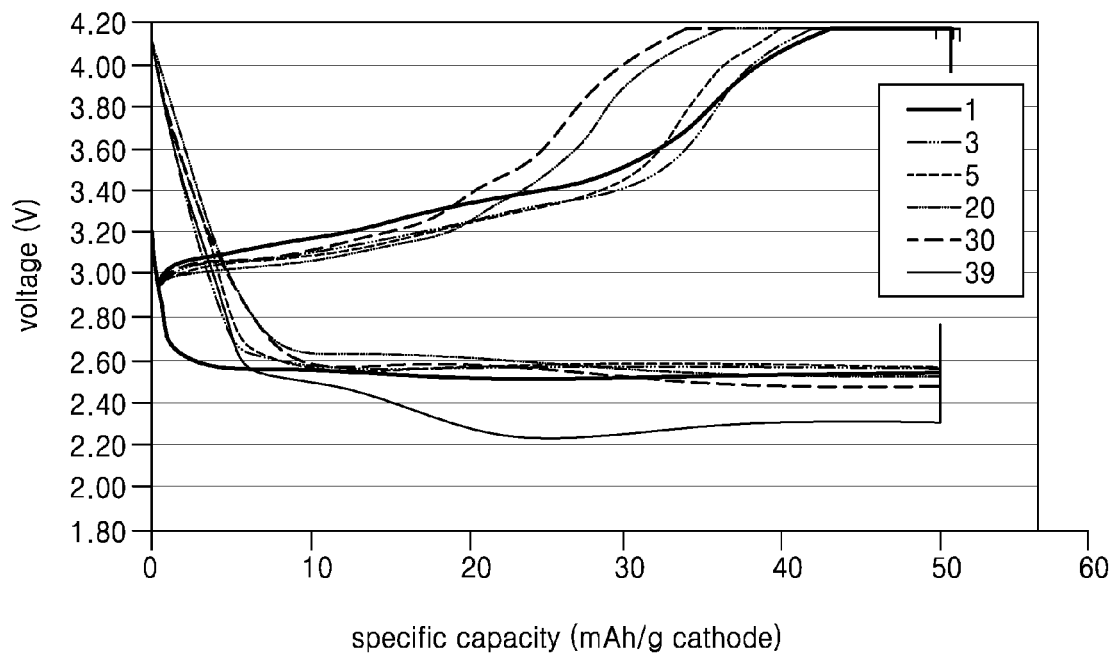

The charge-discharge test results of the lithium air batteries of Example 8 and Comparative Example 8 are shown in FIGS. 6 and 7, respectively. A specific capacity refers to a discharge capacity per total weight of the cathode.

Referring to FIG. 7, in the lithium air battery of Comparative Example 8, a decomposition product-related peak was detected from the 10$^{th}$ cycle. However, in the lithium air battery of Example 8, stable charge-discharge characteristics appeared as shown in FIG. 6, unlike the lithium air battery of Comparative Example 8.

As a result of evaluating discharge capacities of the lithium air batteries of Examples 9 to 14, the lithium air batteries of Examples 9 to 14 were found to have similar charge-discharge characteristics to those of the lithium air battery of Example 8.

Discharge capacities of the lithium air batteries of Comparative Examples 9 to 14 were also evaluated in the same manner as described above with reference to the lithium air batteries of Example 8 and Comparative Example 5. As a result, the lithium air batteries of Comparative Examples 9 to 14 were found to each have a similar discharge capacity to that of the lithium air battery of Comparative Example 8.

As described above, according to the one or more embodiments, an electrolyte including a compound represented by Formula 1 may have improved stability with suppressed decomposition. A lithium air battery with improved charge-discharge characteristics may be manufactured using the electrolyte.

It should be understood that exemplary embodiments described herein should be considered in a descriptive sense only and not for purposes of limitation. Descriptions of features or aspects within each exemplary embodiment should be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An electrolyte for a lithium air battery, the electrolyte comprising a compound represented by Formula 1:

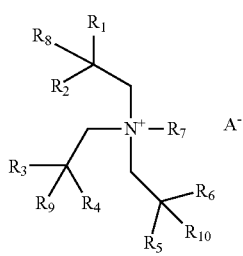

Formula 1 wherein, in Formula 1,
$R_1$ to $R_6$ are each independently a methyl group, an ethyl group, a propyl group, an isopropyl group, an n-butyl group, a tert-butyl group, a sec-butyl group, an isobutyl group, an n-pentyl group, or an isopentyl group,
$R_7$ is a methyl group, an ethyl group, an n-propyl group, an n-butyl group, an n-pentyl group, an n-hexyl group, or an n-octyl group,
$R_8$, $R_9$, and $R_{10}$ are each independently a hydrogen or C1-C10 alkyl group,
a total number of carbons of $R_1$, $R_2$, and $R_8$ is 6 to 30,
a total number of carbons of $R_3$, $R_4$, and $R_9$ is 6 to 30,
a total number of carbons of $R_5$, $R_6$, and $R_{10}$ is 3 to 20; and
$A^-$ is a monovalent anion.

2. The electrolyte of claim 1, wherein $R_8$, $R_9$, and $R_{10}$ are each independently a hydrogen or a methyl group.

3. The electrolyte of claim 1, wherein the compound represented by Formula 1 is a compound represented by Formula 2:

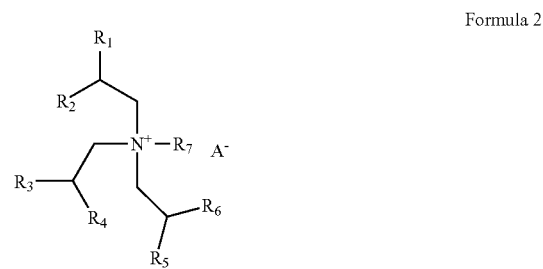

Formula 2 wherein, in Formula 2,
$R_1$ to $R_6$ are each independently a methyl group, an ethyl group, a propyl group, an isopropyl group, an n-butyl group, a tert-butyl group, a sec-butyl group, an isobutyl group, an n-pentyl group, or an isopentyl group,
$R_7$ is a methyl group, an ethyl group, an n-propyl group, an n-butyl group, an n-pentyl group, an n-hexyl group, or an n-octyl group,
a total number of carbons of $R_1$ and $R_2$ is 6 to 20,
a total number of carbons of $R_3$ and $R_4$ is 6 to 20,
a total number of carbons of $R_5$ and $R_6$ is 3 to 20, and
$A^-$ is at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

4. The electrolyte of claim 3, wherein a total number of carbons of $R_5$ and $R_6$ in Formula 2 is 6 to 20.

5. The electrolyte of claim 1, wherein the compound represented by Formula 1 is at least one selected from compounds represented by Formulas 3 to 6:

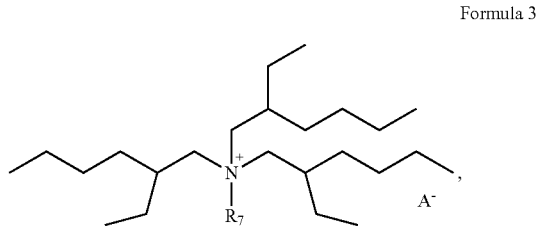

Formula 3

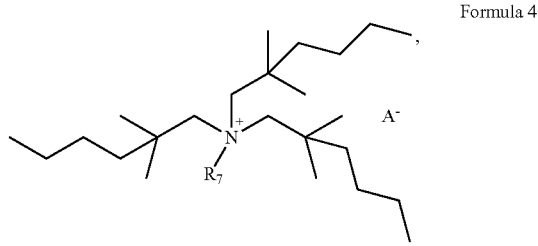

Formula 4

Formula 5

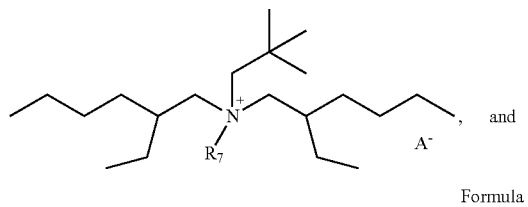

and

Formula 6

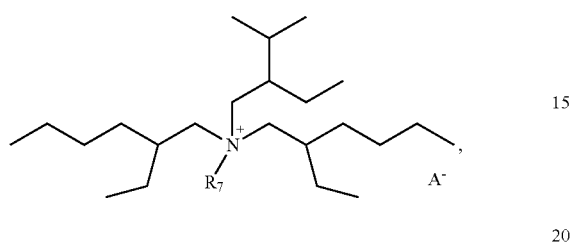

wherein, in Formulas 3 to 6,
R₇ is a C1-C10 alkyl group, and
A⁻ is at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

6. The electrolyte of claim 1, wherein the compound represented by Formula 1 is at least one selected from compounds represented by Formulas 7 to 13:

Formula 7

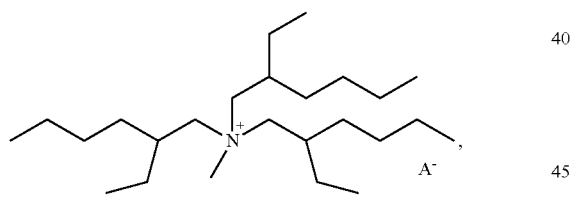

Formula 8

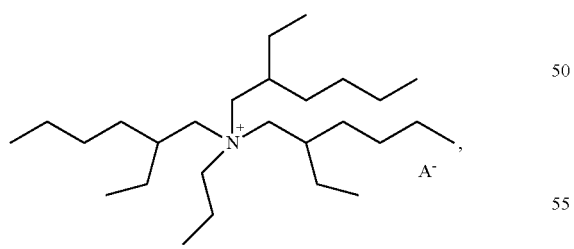

Formula 9

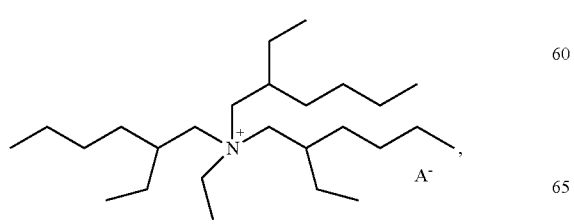

Formula 10

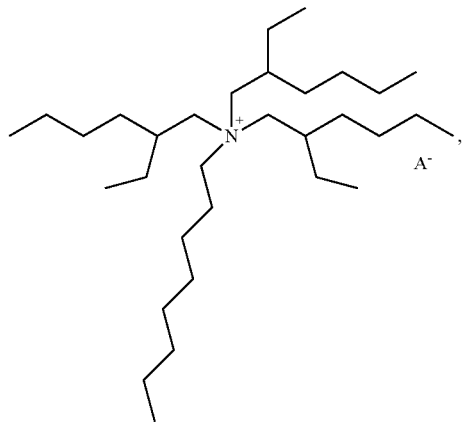

Formula 11

Formula 12

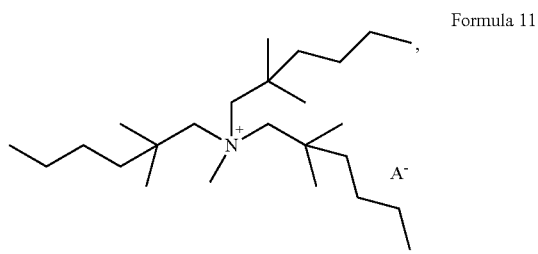

and

Formula 13

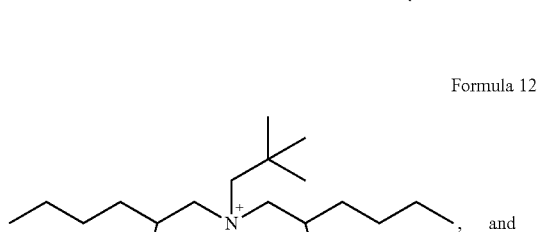

wherein, in Formulas 7 to 13,
A⁻ is at least one selected from $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

7. The electrolyte of claim 1, wherein the compound represented by Formula 1 is at least one selected from compounds represented by Formulas 7a to 13a:

Formula 7a

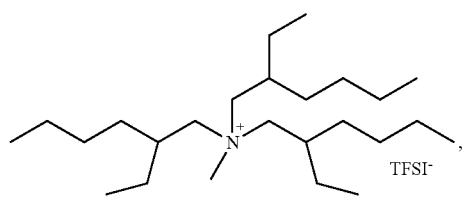

Formula 8a

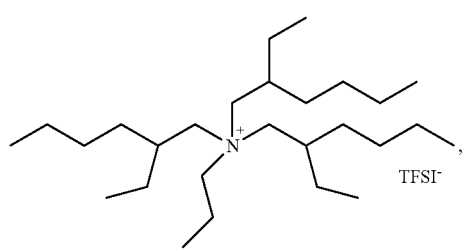

Formula 9a

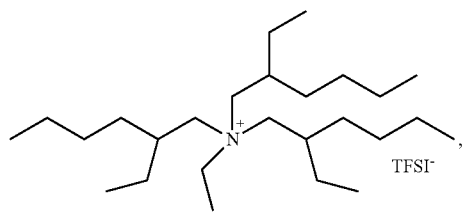

Formula 10a

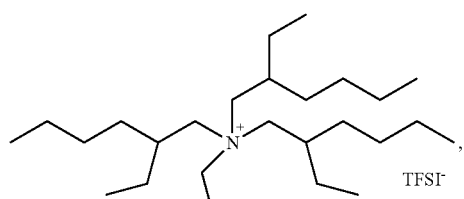

Formula 11a

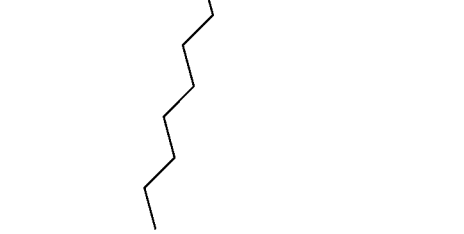

Formula 12a

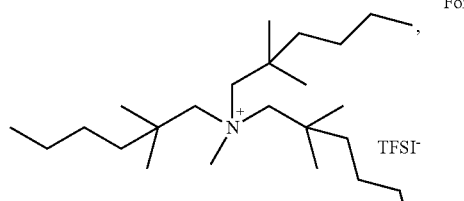, and

Formula 13a

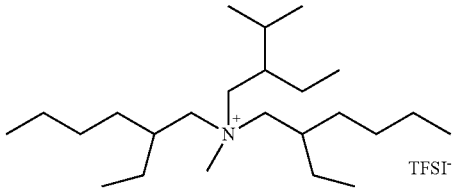

wherein, in Formulas 7a to 13a, TFSI⁻ represents a trifluoromethylsulfonylimide ion.

8. The electrolyte of claim 1, wherein an amount of the compound of Formula 1 is in a range of about 15 parts to about 97 parts by weight, based on 100 parts by weight of a total weight of the electrolyte.

9. The electrolyte of claim 1, further comprising a lithium salt.

10. The electrolyte of claim 9, wherein the lithium salt is at least one selected from $LiPF_6$, $LiBF_4$, $LiSbF_6$, $LiAsF_6$, $LiN(SO_2C_2F_5)_2$, $Li(CF_3SO_2)_2N$, $LiC_4F_9SO_3$, $LiClO_4$, $LiAlO_2$, $LiAlCl_4$, $LiN(C_xF_{2x+1}SO_2)(C_yF_{2y+1}SO_2)$ wherein x and y are natural numbers, LiF, LiBr, LiCl, LiOH, LiI, $LiB(C_2O_4)_2$, lithium bis(oxalato) borate, $Li(FSO_2)_2N$, $Li(CF_3SO_2)_2N$, $Li(C_2F_5SO_2)_2N$, $LiN(C_pF_{2p+1}SO_2)(C_qF_{2q+1}SO_2)$ wherein p and q differ from each other and are each independently an integer of 1 to 20, $LiN((SO_2)_2C_pF_{2p})$ wherein p is an integer selected from 1 to 10, $Li(C_6F_5SO_2)_2N$, $Li(C_{10}F_7SO_2)_2N$, $Li(C_6F_5SO_2)(C_{10}F_7SO_2)N$, $LiN(C_6F_5SO_2)(C_pF_{2p+1}SO_2)$ wherein p is an integer of 1 to 10, and $LiN(C_{10}F_7SO_2)(C_pF_{2p+1}SO_2)$ wherein p is an integer of 1 to 10.

11. The electrolyte of claim 1, wherein the electrolyte further comprises a nonaqueous organic solvent.

12. The electrolyte of claim 1, wherein, when analyzed by liquid chromatography-mass spectrometry a positive ion mode, the electrolyte exhibits a molecular ion peak from mass/atomic number 320 to mass/atomic number 1090.

13. A lithium air battery comprising:
an anode;
a cathode; and
at least one selected from the electrolyte of claim 1 and a reaction product thereof.

14. The lithium air battery of claim 13, wherein the cathode is partially or fully impregnated with the electrolyte.

15. The lithium air battery of claim 13, further comprising a lithium ion-conductive layer between an anode and the electrolyte,
wherein the lithium ion-conductive layer comprises an ion-conductive inorganic particle.

16. The lithium air battery of claim 15, wherein the ion-conductive inorganic particle comprises at least one selected from a glassy active metal ion conductor, an amorphous active metal ion conductor, a ceramic active metal ion conductor, and a glass-ceramic active metal ion conductor.

17. The lithium air battery of claim 15, wherein the ion-conductive inorganic particle is at least one selected from $Li_{1+x+y}Al_xTi_{2-x}Si_yP_{3-y}O_{12}$ wherein $0<x<2$ and $0 \leq y<3$, $BaTiO_3$, $Pb(Zr_aTi_{1-a})O_3$ wherein $0 \leq a \leq 1$, $Pb_{1-x}La_xZr_{1-y}Ti_yO_3$ wherein $0 \leq x<1$ and $0 \leq y<1$, $Pb(Mg_3Nb_{2/3})O_3$—$PbTiO_3$, $HfO_2$, $SrTiO_3$, $SnO_2$, $CeO_2$, $Na_2O$, $MgO$, $NiO$, $CaO$, $BaO$, $ZnO$, $ZrO_2$, $Y_2O_3$, $Al_2O_3$, $TiO_2$, $SiO_2$, SiC, lithium phosphate, $Li_3PO_4$, lithium titanium phosphate, $Li_xTi_y(PO_4)_3$ wherein $0<x<2$ and $0<y<3$, lithium aluminum titanium phosphate, $Li_xAl_yTi_z(PO_4)_3$ wherein $0<x<2$, $0<y<1$, and $0<z<3$), $Li_{1+x+y}(Al_bGa_{1-b})_x(Ti_cGe_{1-c})_{2-x}Si_yP_{3-y}O_{12}$ wherein $0\le x\le 1$, $0\le y\le 1$, $0\le b\le 1$, and $0\le c\le 1$, lithium lanthanum titanate, $Li_xLa_yTiO_3$, wherein $0<x<2$ and $0<y<3$, lithium germanium thiophosphate, $Li_xGe_yP_zS_w$ wherein $0<x<4$, $0<y<1$, $0<z<1$, and $0<w<5$, a lithium nitride, $Li_xN_y$ wherein $0<x<4$ and $0<y<2$, a $SiS_2$ glass, $Li_xSi_yS_z$ wherein $0<x<3$, $0<y<2$, and $0<z<4$, a $P_2S_5$ glass, $Li_xP_yS_z$ wherein $0<x<3$, $0<y<3$, and $0<z<7$, $Li_2O$, $LiF$, $LiOH$, $Li_2CO_3$, $LiAlO_2$, a $Li_2O$—$Al_2O_3$—$SiO_2$—$P_2O_5$—$TiO_2$—$GeO_2$ ceramic, a garnet ceramic, and $Li_{3+x}La_3M_2O_{12}$ wherein $0\le x\le 5$, and M is at least one selected from Te, Nb, and Zr.

18. The lithium air battery of claim 15, further comprising a second electrolyte disposed between the anode and the lithium ion-conductive layer.

19. The lithium air battery of claim 18, wherein the second electrolyte is a solid polymer electrolyte or an inorganic solid electrolyte.

* * * * *